US006998474B1

(12) United States Patent
Icard-Liepkalns et al.

(10) Patent No.: US 6,998,474 B1
(45) Date of Patent: Feb. 14, 2006

(54) POLYPEPTIDES OF THE "BASIC HELIX-LOOP-HELIX" BHLH FAMILY, CORRESPONDING NUCLEIC ACID SEQUENCES

(75) Inventors: Christine Icard-Liepkalns, Tampa, FL (US); Jacques Mallet, Paris (FR); Philippe Ravassard, Paris (FR)

(73) Assignee: Centelion SAS, Vitry-sur-Ceine (FR)

( * ) Notice: Subject to any disclaimer, the term of this patent is extended or adjusted under 35 U.S.C. 154(b) by 514 days.

(21) Appl. No.: 09/595,947

(22) Filed: Jun. 16, 2000

Related U.S. Application Data

(63) Continuation-in-part of application No. 09/331,356, filed as application No. PCT/FR97/02368 on Dec. 19, 1997, now abandoned.

(30) Foreign Application Priority Data

Dec. 19, 1996 (FR) ................... 96 15651

(51) Int. Cl.
*C07N 21/04* (2006.01)
*C12N 5/00* (2006.01)
*C12N 15/00* (2006.01)

(52) U.S. Cl. ................. 536/23.5; 435/325; 435/320.1; 435/69.1; 435/252.3; 530/350; 514/2

(58) Field of Classification Search ............... 536/23.5; 435/325, 320.1, 69.1, 252.3; 530/350; 514/12
See application file for complete search history.

(56) References Cited

U.S. PATENT DOCUMENTS 6,566,496 B1 * 5/2003 Anderson et al. ........... 530/350

FOREIGN PATENT DOCUMENTS

WO    WO 95/30693    11/1995
WO    WO 97/16548    5/1997

OTHER PUBLICATIONS

Bejanin et al. , J. Neurochemistry 58, 1580-1583, 1992.*
Sommer et al., Neurogenins, A Novel Family of Atonal-Related bHLH Transcription Factors, And Putative Mammalian Neuronal Determination Genes That Reveal Progenitor Cell Heterogeneity In The Developing CNS and PNS, Mol. Cell Neurosci. 8(4), 221-241 (1996).
Shimizu et al., MATH-2, A Mammalian Heliz-Loop-Helix Factor Structurally Related To The Product Of *Drosophila* Proneural Gene Atonal, Is Specifically Expressed In The Nervous System, Eur. J. Biochem 229 (1), 239-248 (1995).
Ravassard et al., Relax, A Novel Rat bHLH Transcriptional Regulator Transiently Expressed In The Ventricular Proliferating Zone Of The Developing Central Nervous System, J. Neurosci Res. 48(2), 146-158 (1997).
Gradwohl, M. musculus MATH4B gene, EMBL databank (1996).
Cau et al., Mash1 activates a cascade of bHLH regulators in olfactory neuron progenitors, Development 124, 1611-1621 (1997).
Gradwohl, M. musculus MATH4C gene, GenBank Accession No. Y09166 (Nov. 1997).
Ravassard, P., GenBank Accession No. AJ133776 (Homo sapiens gene for neurogenin 3), (Jun. 1996).
Ravassard, P. et al., GenBank Accession No. CAB45384 (Neurogenin 3 [Homo sapiens]), (Jun. 1996).

* cited by examiner

*Primary Examiner*—Jon Weber
*Assistant Examiner*—Chih-Min Kam
(74) *Attorney, Agent, or Firm*—Synnestvedt & Lechner LLP

(57) ABSTRACT

The present invention relates to nucleic acids that encode novel basic helix-loop-helix polypeptides. The present invention also relates to novel basic helix-loop-helix polypeptides, in particular, rat Relax and human ngn3 polypeptides. The invention also relates to methods for the detection of nucleic acids and polypeptides according to the invention. The invention also relates to methods for the detection of activators or inhibitors of the polypeptides of the invention. Finally, the present invention relates to methods of prevention and/or treatment of pathologies, dysfunctions, disorders or conditions affecting the nervous system.

17 Claims, 7 Drawing Sheets

```
  R    G    V    L    P    T    F    P    D    D    A    K    L    T    K    I    E    T      18
 CGC  GGT  GTC  CTG  CCC  ACC  TTC  CCG  GAT  GAC  GCC  AAA  CTT  ACA  AAG  ATC  GAG  ACC     54
                                                                        ⇐
  L    R    F    A    L    N    Y    I    W    A    L    T    Q    T    L    R    I    A      36
 CTG  CGC  TTC  GCC  CTC  AAC  TAC  ATT  TGG  GCA  CTG  ACT  CAG  ACG  CTG  CGC  ATA  GCG    108
 ─────────── CIG3'_2
  D    H    S    F    Y    G    P    E    P    P    V    P    C    G    E    L    G    S      54
 GAC  CAC  AGC  TTC  TAC  GGC  CCC  GAG  CCC  CCT  GTG  CCC  TGT  GGG  GAG  CTG  GGA  AGC    162
           ⇐ ─────────────── CIG3'_1
  P    G    G    G    S    S    G    D    W    G    S    I    Y    S    P    V    S    Q      72
 CCG  GGA  GGG  GGC  TCC  AGC  GGC  GAC  TGG  GGC  TCT  ATC  TAC  TCC  CCA  GTT  TCC  CAA    216
                          ⇐ ───────────────── CIG3'_0
  A    G    S    L    S    P    T    A    S    L    E    E    F    P    G    L    Q    V      90
 GCT  GGT  AGC  CTG  AGC  CCC  ACA  GCC  TCA  TTG  GAG  GAG  TTC  CCT  GGC  CTG  CAG  GTG    270

P    S    S    P    S    C    L    L    P    G    T    L    V    F    S    D    F    L     108
 CCC  AGC  TCC  CCA  TCC  TGT  CTG  CTC  CCG  GGC  ACC  CTG  GTG  TTC  TCA  GAC  TTC  TTG    324

*                                                                                            109
 TGA  agggcccaaacaggccctgggcggtgggcgctggcagaaagggagggagtcagagctgtctgaaatg                     394 gaaggtagtggaggcactcgagcatctcgccccttctggctttcattagtcaggtccctgatttaaccagga                     466 ttcgcacagttccttgctgctgtgcgtgcacaaaggacattgcaggctgatctcctcttaaccctcctcagt                     538 gtggccacctcaaactcccgctccaagcagaggagagccgtagcactaaatagttgggagactcccatactt                     610 cctggtgactccgccctctttcaaatctgcgggcctccaaccaccgctttctccagagtgacctaatccagt                     682 gttgcgtcttacctcactggctcttgttccata                                                            715
```

FIG. 1

|          | basic                                    | Helix-I                  |     |
|----------|------------------------------------------|--------------------------|-----|
| Relax    | S R R K K A N D R E R N R M H N L N S A L D A L R G V L E T | 112 |
| Math-1   | Q R R L A A N A R E R R R M H G L N H A F D Q L R N V I E S | 185 |
| Neurod   | L R R M K A N A R E R N R M H G L N A A L D N L R K V V P C | 58  |
| Mash1    | A A V A R R N E R E R N R H V K L V N L G F A T L R E H V P N | 142 |

|          | Loop           | Helix-2                  |     |
|----------|----------------|--------------------------|-----|
| Relax    | F P D D A K L T K I E T L R F A H N Y I W A L T Q T L R I A | 142 |
| Math-1   | F N N D K K L S K Y E T L Q M A Q I Y I N A L S E L L Q T P | 215 |
| Neurod   | Y S K T Q K L S K I E T L R L A K N Y I W A L S E I L R S G | 88  |
| Mash1    | G A A N K K M S K V E T L R S A V Q Y I R A L Q Q L L D E H | 172 |

FIG 2

```
cctcggaccccattctctcttcttttctcctttggggctggggcaactcccaggcgggggcgcctgcagctc      72
agctgaacttggcgaccagaagcccgctgagctccccacggccctcgctgctcatcgctctctattcttttg    144
cgccggtagaaaggtaatatttggaggccttcgaggggacgggcaggggaaagagggatcctctgacccagcg   216
ggggctgggaggatggctgttttgttttttcccacctagcctcggaatcgcggactgcgccgtgacggact    288
```

```
                                         M   T   P   Q   P   S   G   A   P      9
caaacttacccttccctctgaccccgccgtagg ATG ACG CCT CAA CCC TCG GGT GCG CCC       348
  T   V   Q   V   T   R   E   T   E   R   S   F   P   R   A   S   E   D     27
 ACT GTC CAA GTG ACC CGT GAG ACG GAG CGG TCC TTC CCC AGA GCC TCG GAA GAC    402
  E   V   T   C   P   T   S   A   P   P   S   P   T   R   T   P   G   N     45
 GAA GTG ACC TGC CCC ACG TCC GCC CCG CCC AGC CCC ACT CGC ACA CCG GGG AAC    456
  C   A   E   A   E   E   G   G   C   R   G   A   P   R   K   L   R   A     63
 TGC GCA GAG GCG GAA GAG GGA GGC TGC CGA GGG GCC CCG AGG AAG CTC CGG GCA    510
  R   R   G   G   R   S   R   P   K   S   E   L   A   L   S   K   Q   R     81
 CGG CGC GGG GGA CGC AGC CGG CCT AAG AGC GAG TTG GCA CTG AGC AAG CAG CGA    564
  R   S   R   K   K   A   N   D   R   E   R   N   R   M   H   D   L         99
 CGG AGT CGG CGA AAG AAG GCC AAC GAC CGC GAG CGC AAT CGA ATG CAC GAC CTC    618
  N   S   A   L   D   A   L   R   G   V   L   P   T   F   P   D   D   A    117
 AAC TCG GCA CTG GAC GCC CTG CGC GGT GTC CTG CCC ACC TTC CCA GAC GAC GCG    672
  K   L   T   K   I   E   T   L   R   F   A   H   N   Y   I   W   A   L    135
 AAG CTC ACC AAG ATC GAG ACG CTG CGC TTC GCC CAC AAC TAC ATC TGG GCG CTG    726
```

```
  T   Q   T   L   R   I   A   D   H   S   L   Y   A   L   E   P   P   A    153
 ACT CAA ACG CTG CGC ATA GCG GAC CAC AGC TTG TAC GCG CTG GAG CCG CCG GCG    780
```

```
  P   H   C   G   E   L   G   S   P   G   G   P   P   G   D   W   G   S    171
 CCG CAC TGC GGG GAG CTG GGC AGC CCA GGC GGT CCC CCC GGG GAC TGG GGG TCC    834
  L   Y   S   P   V   S   Q   A   G   S   L   S   P   A   A   S   L   E    189
 CTC TAC TCC CCA GTC TCC CAG GCT GGC AGC CTG AGT CCC GCC GCG TCG CTG GAG    888
  E   R   P   G   L   L   G   A   T   S   S   A   C   L   S   P   G   S    207
 GAG CGA CCC GGG CTG CTG GGG GCC ACC TCT TCC GCC TGC TTG AGC CCA GGC AGT    942
  L   A   F   S   D   F   L                                                 214
 CTG GCT TTC TCA GAT TTT CTG tgaaaggacctgtctgtcgctgggctgtgggtgctaagggtaa   1006
gggagagggagggagccggagccgtagagggtggccgacggcggcggccctcaaaagcacttgttccttct   1078
gcttctccctagctgaccctggccggcccaggcctccacgggggcggtaggctgggttcattccccggccc   1150
tccgagccgcgccaacgcacgcaaccttgctgctgcccgcgcgaagtgggcattgcaaagtgcgctcattt   1222
taggcctcctctctgccaccacccataatcccattcaaagaatactagaatggtagcactacccggccgga   1294
gccgccaccgtcttgggtcgccctaccctcactca                                       1330
```

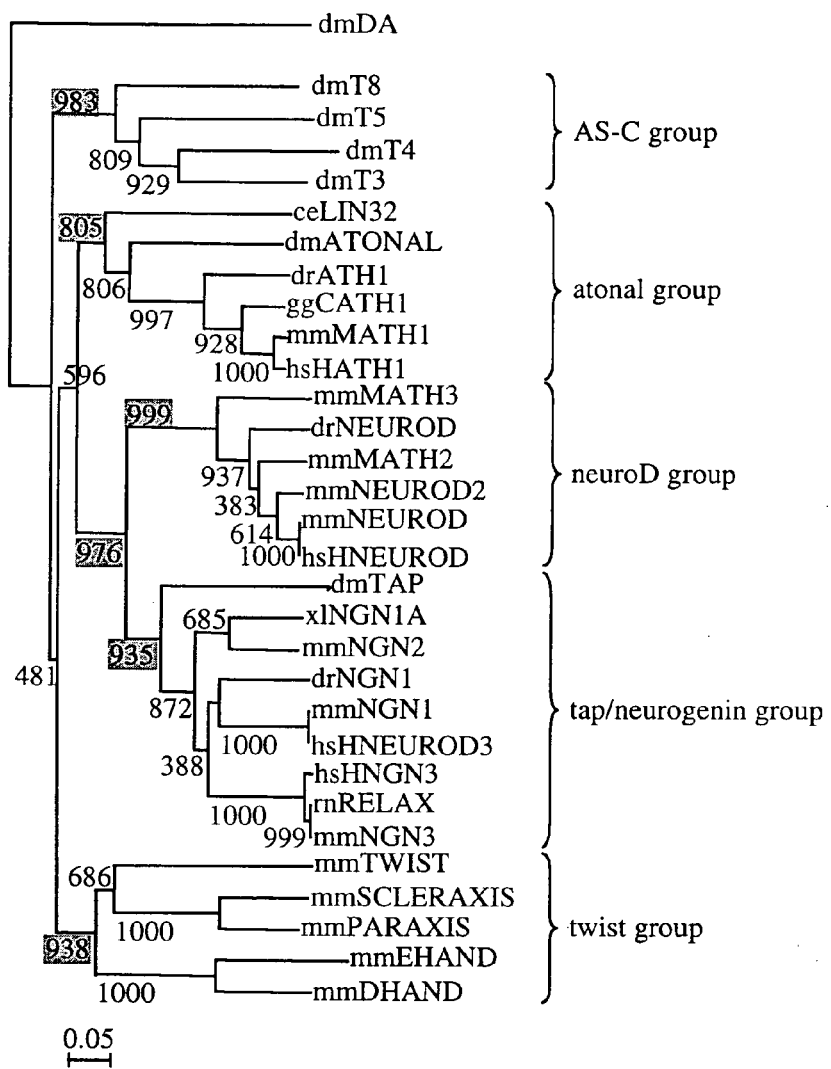
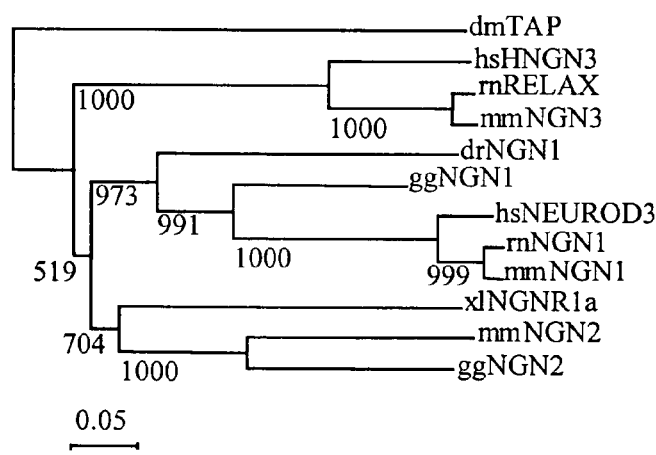
FIG 5

SEQUENCE LISTING

<160> NUMBER OF SEQ ID NOS: 40

<210> SEQ ID NO 1
<211> LENGTH: 1460
<212> TYPE: DNA
<213> ORGANISM: Rattus norvegicus

<400> SEQUENCE: 1

```
gcaggtagcg agaggagcag tccctgggcc cccgttgctg attggcccgt ggcacaggca      60
gcagcccggc aggcacgctc ctggtccggg cagagcagat aaagcgtgcc aggggacaca     120
cgattagcag ctcagaagtc cctctgggtc tcaccactgc acagaggccg aggacccct      180 ccgagcttct ttgctgcctc cagacgcaat ttactccagg cgagggcgcc tgcagctcag     240
caaaacttcg aagcgagcag aggggttcag ctatccaccg ctgcttgact ctgaccaccc     300
gcagctctct gttcttttga gcccggagta actaggtaac atttaggaac ctccaaaggg     360
```

```
tagaagaggg gagtgggtgg gcgtactcta gtcccgcgtg gagtgacctc taagtcagag       420
actgtcacac cccccttcca ttttttccca acctcaggat ggcgcctcat cccttggatg       480
cgcccaccat ccaagtgtcc caagagaccc agcaacccct tcccggagcc tcggaccacg       540
aagtgctcag ttccaattcc accccaccta gccccactct cgtaccgagg gactgctccg       600
aagcagaagc aggtgactgc cgagggacat cgaggaagct ccgtgcgcgg cgcggagggc       660
gcaacaggcc caagagcgag ttggcactga gcaagcagcg acgaagccgg cgcaagaagg       720
ccaacgaccg ggagcgcaac cgcatgcaca accttaactc cgcgctggat gcgctgcgcg       780
gtgtcctgcc caccttcccg gatgacgcca aacttacaaa gatcgagacc ctgcgcttcg       840
cccacaacta catttgggca ctgactcaga cgctgcgcat agcggaccac agcttctacg       900
gccccgagcc ccctgtgccc tgtggggagc tgggaagccc gggagggggc tccagcggcg       960
actggggctc tatctactcc ccagtttccc aagctggtag cctgagcccc acagcctcat      1020
tggaggagtt ccctggcctg caggtgccca gctccccatc ctgtctgctc ccgggcaccc      1080
tggtgttctc agacttcttg tgaagggccc aaacaggccc tgggcggtgg gcgctggcag      1140
aaagggaggg agtcagagct gtctgaaatg gaaggtagtg gaggcactcg agcatctcgc      1200
cccttctggc tttcattagt caggtccctg atttaaccag gattcgcaca gttccttgct      1260
gctgtgcgtg cacaaaggat attgcaggct gatctcctct taaccctcct cagtgtggcc      1320 acctcaaaact cccgctccaa gcagaggaga gccgtagcac taaatagttg ggagactccc      1380
atacttcctg gtgactccgc cctctttcaa atctgcgggc ctccaaccac cgctttctcc      1440
agagtgacct aatccagtgt                                                  1460

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: PCR Primer
<220> FEATURE:
<223> OTHER INFORMATION: n = Inosine

<400> SEQUENCE: 2
aatkhgmgng agcgcndkcg cryg                                              24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: PCR Primers

<400> SEQUENCE: 3
ggcsrdtytc agggtsybga yctt                                              24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: PCR Primers

<400> SEQUENCE: 4
aaccttaact ccgcgctgga tgcgc                                             25

<210> SEQ ID NO 5
```

```
<211> LENGTH: 18
<212> TYPE: DNA
<213> ORGANISM: Artificial Sequence
<220> FEATURE:
<223> OTHER INFORMATION: Description of Artificial Sequence: PCR Primers

<400> SEQUENCE: 5
cgcggtgtcc tgcccacc                                                   18

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: E box

<400> SEQUENCE: 6 caggtg                                                                 6

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Mutated E
      box

<400> SEQUENCE: 7 tccgtg                                                                 6

<210> SEQ ID NO 8
<211> LENGTH: 214
<212> TYPE: PRT
<213> ORGANISM: Rattus norvegicus

<400> SEQUENCE: 8
```

Met Ala Pro His Pro Leu Asp Ala Pro Thr Ile Gln Val Ser Gln Glu
 1               5                  10                  15

Thr Gln Gln Pro Phe Pro Gly Ala Ser Asp His Glu Val Leu Ser Ser
            20                  25                  30

Asn Ser Thr Pro Pro Ser Pro Thr Leu Val Pro Arg Asp Cys Ser Glu
        35                  40                  45

Ala Glu Ala Gly Asp Cys Arg Gly Thr Ser Arg Lys Leu Arg Ala Arg
    50                  55                  60

Arg Gly Gly Arg Asn Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Ser Gly Asp Trp Gly Ser Ile Tyr Ser Pro Val
                165                 170                 175

Ser Gln Ala Gly Ser Leu Ser Pro Thr Ala Ser Leu Glu Glu Phe Pro
            180                 185                 190

```
Gly Leu Gln Val Pro Ser Ser Pro Ser Cys Leu Leu Pro Gly Thr Leu
        195                 200                 205

Val Phe Ser Asp Phe Leu
    210
```

<210> SEQ ID NO 9
<211> LENGTH: 1330
<212> TYPE: DNA
<213> ORGANISM: Homo sapiens

<400> SEQUENCE: 9

```
cctcggaccc cattctctct tcttttctcc tttggggctg gggcaactcc caggcggggg      60
cgcctgcagc tcagctgaac ttggcgacca gaagcccgct gagctcccca cggccctcgc     120
tgctcatcgc tctctattct tttgcgccgg tagaaaggta atatttggag gccttcgagg     180
gacgggcagg ggaaagaggg atcctctgac ccagcggggg ctgggaggat ggctgttttt     240
gttttttccc acctagcctc ggaatcgcgg actgcgccgt gacggactca aacttaccct     300
tccctctgac cccgccgtag gatgacgcct caaccctcgg gtgcgcccac tgtccaagtg     360
acccgtgaga cggagcggtc cttccccaga gcctcggaag acgaagtgac ctgccccacg     420
tccgccccgc ccagccccac tcgcacaccg gggaactgcg cagaggcgga gagggaggc     480
tgccgagggg ccccgaggaa gctccgggca cggcgcgggg gacgcagccg gcctaagagc     540
gagttggcac tgagcaagca gcgacggagt cggcgaaaga aggccaacga ccgcgagcgc     600
aatcgaatgc acgacctcaa ctcggcactg gacgccctgc gcggtgtcct gcccaccttc     660
ccagacgacg cgaagctcac caagatcgag acgctgcgct tcgcccacaa ctacatctgg     720
gcgctgactc aaacgctgcg catagcggac acacagcttgt acgcgctgga gccgccggcg     780
ccgcactgcg gggagctggg cagcccaggc ggtcccccg gggactgggg gtccctctac     840
tccccagtct cccaggctgg cagcctgagt cccgccgcgt cgctggagga gcgacccggg     900
ctgctggggg ccacctcttc cgcctgcttg agcccaggca gtctggcttt ctcagatttt     960
ctgtgaaagg acctgtctgt cgctgggctg tgggtgctaa gggtaaggga gagggagga    1020
gccgggagcc gtagagggtg gccgacggcg gcggccctca aaagcacttg ttccttctgc    1080
ttctccctag ctgaccctg gccggcccag gcctccacgg gggcggtagg ctgggttcat    1140
tccccggccc tccgagccgc gccaacgcac gcaaccttg ctgctgcccg cgcgaagtgg    1200
gcattgcaaa gtcgcgctcat tttaggcctc ctctctgcca ccaccccata atcccattca    1260
aagaatacta gaatggtagc actacccggc cggagccgcc caccgtcttg ggtcgcccta    1320
ccctcactca                                                          1330
```

<210> SEQ ID NO 10
<211> LENGTH: 214
<212> TYPE: PRT
<213> ORGANISM: Homo sapiens

<400> SEQUENCE: 10

```
Met Thr Pro Gln Pro Ser Gly Ala Pro Thr Val Gln Val Thr Arg Glu
  1               5                  10                  15

Thr Glu Arg Ser Phe Pro Arg Ala Ser Glu Asp Glu Val Thr Cys Pro
             20                  25                  30

Thr Ser Ala Pro Pro Ser Pro Thr Arg Thr Pro Gly Asn Cys Ala Glu
         35                  40                  45

Ala Glu Glu Gly Gly Cys Arg Gly Ala Pro Arg Lys Leu Arg Ala Arg
     50                  55                  60
```

-continued

```
Arg Gly Gly Arg Ser Arg Pro Lys Ser Glu Leu Ala Leu Ser Lys Gln
 65                  70                  75                  80

Arg Arg Ser Arg Arg Lys Lys Ala Asn Asp Arg Glu Arg Asn Arg Met
                 85                  90                  95

His Asp Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Leu Tyr Ala Leu Glu Pro Pro Ala Pro His Cys Gly Glu Leu Gly
145                 150                 155                 160

Ser Pro Gly Gly Pro Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Ser Ser Ala Cys Leu Ser Pro Gly Ser Leu
        195                 200                 205

Ala Phe Ser Asp Phe Leu
    210
```

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 11
caacgaccgg cagcgcaa                                                18

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 12
gcccagatgt agttgtgggc gaag                                         24

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: PCR Primer
<220> FEATURE:
<223> OTHER INFORMATION: n = a, c, t, or g

<400> SEQUENCE: 13
atcgttgaga ctcgtaccag cagagtcacg agagagacta cacggtactg gnnnnnnnnn  60

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 14
agacgacgcg aagctcacca                              20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 15
gctcaccaag atcgagacgc tgcg                         24

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 16
atcgttgaga ctcgtaccag cagag                        25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 17
tcgtaccagc agagtcacga gagag                        25

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 18
ctgccagcct gggagactg                               19

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: PCR Primer

<400> SEQUENCE: 19
ctgcatctat ctaatgctcc tctcgctacc tgctcactct gcgtgacatc    50

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 20
gatgtcacgc agagtgagca ggtag                        25

<210> SEQ ID NO 21
<211> LENGTH: 23
<212> TYPE: DNA
<213> ORGANISM: Artificial Sequence

```
<220> FEATURE:
<223> OTHER INFORMATION: Description of Artificial Sequence: PCR Primer

<400> SEQUENCE: 21
agcctgggag actggggagt aga                                              23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 22
agagtgagca ggtagcgaga ggag                                             24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 23
cgctatgcgc agcgtttgag tc                                               22

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 24
cctcggaccc cattctctct tcttt                                            25

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 25
tgagtgaggg tagggcgacc caag                                             24

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 26
aggaagctcc gggca                                                       15

<210> SEQ ID NO 27
<211> LENGTH: 1381
<212> TYPE: RNA
<213> ORGANISM: Artificial Sequence
<220> FEATURE:
<223> OTHER INFORMATION: Description of Artificial Sequence: Probe

<400> SEQUENCE: 27
gggcgaauug ggcccgacgu cgcaugcucc cggccgccau ggccgcggga uuugagugag      60
```

-continued

| | |
|---|---|
| gguagggcga cccaagacgg ugggcggcuc cggccgggua gugcuaccau ucuaguauuc | 120 |
| uuugaauggg auuauggggu ggugggcagag aggaggccua aaaugagcgc acuuugcaau | 180 |
| gcccacuucg cgcgggcagc agcaagggu gcgugcguug gcgcggcucg gagggccggg | 240 |
| gaaugaaccc agccuaccgc ccccguggag gccugggccg gccaggdguc agcuagggag | 300 |
| aagcagaagg ascaagugcu uuugagggcc gccsccgucg gccacccucu acggcucccg | 360 |
| gcucccuccc ucucccuuac ccuuagcacc cacagcccag cgacagacag guccuuucac | 420 |
| agaaaaucug agaaagccag acugccuggg cucaagcagg cggaagaggu ggcccccagc | 480 |
| agcccgdguc gcuccuccag cgacgcgcg ggacucaggc ugccagccug ggagacuggg | 540 |
| gaguagaggg accccccaguc cccgggggga ccgccugggc ugcccagcuc cccgcagugc | 600 |
| ggcgccggcg gcuccagcgc guacaagcug ugguccgcua ugcgcagcgu uugagucagc | 660 |
| gcccagaugu aguuguggc gaagcgcagc gucucgaucu uggugagcuu cgcgucgucu | 720 |
| gggaaggugu gcaggacacc gcgcagggcg uccagugccg aguugagguc gugcauucga | 780 |
| uugcgcucgc ggucguuggc cuucuuucgc cgacuccguc gcugcuugcu cagugccaac | 840 |
| ucgcucuuag gccggcugcg uccccgcgc cgugcccgga gcuuccucgg ggccccucgg | 900 |
| cagccucccu cuuccgccuc ugcgcaguuc cccggugugc gagugggcu gggcggggcg | 960 |
| gacgugggc aggucacuuc gucuuccgag gcucugggga aggaccgcuc cgucucacgg | 1020 |
| ucacuuggac aguggcgca cccgagggu gaggcgucau ccuacggcgg ggucagaggg | 1080 |
| aagdguaagu uugaguccgu cacggcgcag uccgcgauuc cgaggcuagg ugdgaaaaaa | 1140 |
| caaaaacagc cauccuccca gccccgcug ggucagagga ucccucuuuc ccugcccgu | 1200 |
| cccucgaagg ccuccaaaua uuaccuuucu accggcgcaa aagaauagag agcgaugagc | 1260 |
| agcgagggcc gugggagcu cagcgggcuu cuggucgcca aguucagcug agcugcaggc | 1320 |
| gcccccgccu gggaguugcc ccagccbcaa aggagaaaag aagagagaau ggggguccgag | 1380 |
| g | 1381 |

<210> SEQ ID NO 28
<211> LENGTH: 1427
<212> TYPE: RNA
<213> ORGANISM: Artificial Sequence
<220> FEATURE:
<223> OTHER INFORMATION: Description of Artificial Sequence: Probe

<400> SEQUENCE: 28

| | |
|---|---|
| agcuaugcau ccaacgcguu gggagcucuc ccauauggu gaccugcagg cggccgcgaa | 60 |
| uucacuagug auuccucgga ccccauucuc ucuucuuuuc uccuuugggg cugggcaac | 120 |
| ucccaggcgg gggcgccugc agcucagcug aacuuggcga ccagaagccc gcugagcucc | 180 |
| ccacggcccu cgcugcucau cgcucucuau ucuuuugcgc cgguagaaag guaauauuug | 240 |
| gaggccuucg agggacgggc aggggaaaga gggauccucu gacccagcgg gggcugggag | 300 |
| gauggcuguu uuuguuuuuu cccaccuagc cucggaaucg cggacugcgc cgugacggac | 360 |
| ucaaacuuac ccuuccccucu gacccgccg uaggaugacg ccucaacccu cgggugcgcc | 420 |
| cacuguccaa gugacccgug agacggagcg guccuucccc agagccucgg aagacgaagu | 480 |
| gaccugcccc acgucccgccc cgcccagccc cacucgcaca ccggggaacu gcgcagaggc | 540 |
| ggaagaggga ggcugccgag gggccccgag gaagcuccgg gcacggcgcg ggggacgcag | 600 |
| ccggccuaag agcgaguugg cacugagcaa gcagcgacgg agucggcgaa agaaggccaa | 660 |
| cgaccgcgag cgcaaucgaa ugcacgaccu caacucggca cuggacgccc ugcgcggugu | 720 |

```
ccugcccacc uucccagacg acgcgaagcu caccaagauc gagacgcugc gcuucgccca    780
caacuacauc ugggcgcuga cucaaacgcu gcgcauagcg gaccacagcu uguacgcgcu    840
ggagccgccg gcgccgcacu gcggggagcu gggcagccca gcggucccc ccggggacug     900 gggguccuc uacuccccag ucuccaggc uggcagccug aguccgccg cgucgcugga      960 ggagcgaccc gggcugcugg gggccaccuc uuccgccugc uugagcccag gcagucuggc   1020
uuucucagau uuucugugaa aggaccuguc ugucgcuggg cuguggugc uaaggguaag    1080 ggagaggggag ggagccggga gccguagagg guggccgacg gcggcggccc ucaaaagcac  1140
uuguuccuuc ugcuucuccc uagcugaccc cuggccggcc caggccucca cggggggcggu  1200 aggcugggu cauuccccgg cccuccgagc gcgccaacg cacgcaaccc uugcugcugc     1260
ccgcgcgaag ugggcauugc aaagugcgcu cauuuuaggc cuccucucug ccaccacccc   1320 auaauccau ucaaagaaua cuagaauggu agcacuaccc ggccggagcc gcccaccguc    1380
uugggucgcc cuacccucac ucaaaucgaa uucccgcggc cgccaug                 1427
```

<210> SEQ ID NO 29
<211> LENGTH: 715
<212> TYPE: DNA
<213> ORGANISM: Rattus norvegicus

<400> SEQUENCE: 29

```
cgcggtgtcc tgcccacctt cccggatgac gccaaactta caaagatcga gaccctgcgc    60
ttcgccctca actacatttg ggcactgact cagacgctgc gcatagcgga ccacagcttc   120
tacggccccg agccccctgt gccctgtggg gagctgggaa gcccgggagg gggctccagc    180
ggcgactggg gctctatcta ctccccagtt tcccaagctg gtagcctgag ccccacagcc   240
tcattggagg agttccctgg cctgcacgtg cccagctccc catcctatct gctcccgggc   300
accctggtgt tctcagactt cttgtgaagg gcccaaacag gccctgggcg gtgggcgctg   360
gcagaaaggg agggagtcag agctgtctga aatggaaggt agtggaggca ctcgagcatc   420 tcgcccttc tggctttcat tagtcaggtc cctgatttaa ccaggattcg cacagttcct    480
tgctgctgtg cgtgcacaaa ggacattgca ggctgatctc ctcttaaccc tcctcagtgt   540
ggccacctca aactcccgct ccaagcagag gagagccgta gcactaaata gttgggagac   600
tcccatactt cctggtgact ccgccctctt tcaaatctgc gggcctccaa ccaccgcttt   660
ctccagagtg acctaatcca gtgttgcgtc ttacctcact ggctcttgtt ccata        715
```

<210> SEQ ID NO 30
<211> LENGTH: 108
<212> TYPE: PRT
<213> ORGANISM: Rattus norvegicus

<400> SEQUENCE: 30

```
Arg Gly Val Leu Pro Thr Phe Pro Asp Asp Ala Lys Leu Thr Lys Ile
 1               5                  10                  15

Glu Thr Leu Arg Phe Ala Leu Asn Tyr Ile Trp Ala Leu Thr Gln Thr
            20                  25                  30

Leu Arg Ile Ala Asp His Ser Phe Tyr Gly Pro Glu Pro Pro Val Pro
        35                  40                  45

Cys Gly Glu Leu Gly Ser Pro Gly Gly Gly Ser Ser Gly Asp Trp Gly
    50                  55                  60

Ser Ile Tyr Ser Pro Val Ser Gln Ala Gly Ser Leu Ser Pro Thr Ala
65                  70                  75                  80
```

```
Ser Leu Glu Glu Phe Pro Gly Leu Gln Val Pro Ser Ser Pro Ser Cys
                85                  90                  95

Leu Leu Pro Gly Thr Leu Val Phe Ser Asp Phe Leu
            100                 105

<210> SEQ ID NO 31
<211> LENGTH: 60
<212> TYPE: PRT
<213> ORGANISM: Rattus norvegicus

<400> SEQUENCE: 31

Ser Arg Arg Lys Lys Ala Asn Asp Arg Glu Arg Asn Arg Met His Asn
1               5                   10                  15

Leu Asn Ser Ala Leu Asp Ala Leu Arg Gly Val Leu Pro Thr Phe Pro
                20                  25                  30

Asp Asp Ala Lys Leu Thr Lys Ile Glu Thr Leu Arg Phe Ala His Asn
            35                  40                  45

Tyr Ile Trp Ala Leu Thr Gln Thr Leu Arg Ile Ala
    50                  55                  60

<210> SEQ ID NO 32
<211> LENGTH: 60
<212> TYPE: PRT
<213> ORGANISM: Mus musculus

<400> SEQUENCE: 32

Gln Arg Arg Leu Ala Ala Asn Ala Arg Glu Arg Arg Arg Met His Gly
1               5                   10                  15

Leu Asn His Ala Phe Asp Gln Leu Arg Asn Val Ile Pro Ser Phe Asn
                20                  25                  30

Asn Asp Lys Lys Leu Ser Lys Tyr Glu Thr Leu Gln Met Ala Gln Ile
            35                  40                  45

Tyr Ile Asn Ala Leu Ser Glu Leu Leu Gln Thr Pro
    50                  55                  60

<210> SEQ ID NO 33
<211> LENGTH: 60
<212> TYPE: PRT
<213> ORGANISM: Mus musculus

<400> SEQUENCE: 33

Leu Arg Arg Met Lys Ala Asn Ala Arg Glu Arg Asn Arg Met His Gly
1               5                   10                  15

Leu Asn Ala Ala Leu Asp Asn Leu Arg Lys Val Val Pro Cys Tyr Ser
                20                  25                  30

Lys Thr Gln Lys Leu Ser Lys Ile Glu Thr Leu Arg Leu Ala Lys Asn
            35                  40                  45

Tyr Ile Trp Ala Leu Ser Glu Ile Leu Arg Ser Gly
    50                  55                  60

<210> SEQ ID NO 34
<211> LENGTH: 60
<212> TYPE: PRT
<213> ORGANISM: Mus musculus

<400> SEQUENCE: 34

Ala Ala Val Ala Arg Arg Asn Glu Arg Glu Arg Asn Arg Val Lys Leu
1               5                   10                  15

Val Asn Leu Gly Phe Ala Thr Leu Arg Glu His Val Pro Asn Gly Ala
```

```
            20                  25                  30
Ala Asn Lys Lys Met Ser Lys Val Glu Thr Leu Arg Ser Ala Val Gln
        35                  40                  45

Tyr Ile Arg Ala Leu Gln Gln Leu Leu Asp Glu His
    50                  55                  60

<210> SEQ ID NO 35
<211> LENGTH: 237
<212> TYPE: PRT
<213> ORGANISM: Homo sapiens

<400> SEQUENCE: 35

Met Pro Ala Arg Leu Glu Thr Cys Ile Ser Asp Leu Asp Cys Ala Ser
1               5                   10                  15

Ser Ser Gly Ser Asp Leu Ser Gly Phe Leu Thr Asp Glu Glu Asp Cys
                20                  25                  30

Ala Arg Leu Gln Gln Ala Ala Ser Ala Ser Gly Pro Pro Ala Pro Ala
            35                  40                  45

Arg Arg Ser Ala Pro Asn Ile Ser Arg Ala Ser Glu Val Pro Gly Ala
        50                  55                  60

Gln Asp Asp Glu Gln Glu Arg Arg Arg Arg Gly Arg Thr Arg Val
65                  70                  75                  80

Arg Ser Glu Ala Leu Leu His Ser Leu Arg Arg Ser Arg Val Lys
                85                  90                  95

Ala Asn Asp Arg Glu Arg Asn Arg Met His Asn Leu Asn Ala Ala Leu
            100                 105                 110

Asp Ala Leu Arg Ser Val Leu Pro Ser Phe Pro Asp Asp Thr Lys Leu
        115                 120                 125

Thr Lys Ile Glu Thr Leu Arg Phe Ala Tyr Asn Tyr Ile Trp Ala Leu
    130                 135                 140

Ala Glu Thr Leu Arg Leu Ala Asp Gln Gly Leu Pro Gly Gly Gly Ala
145                 150                 155                 160

Arg Glu Arg Leu Leu Pro Pro Gln Cys Val Pro Cys Leu Pro Gly Pro
                165                 170                 175

Pro Ser Pro Ala Ser Asp Ala Glu Ser Trp Gly Ser Gly Ala Ala Ala
            180                 185                 190

Ala Ser Pro Leu Ser Asp Pro Ser Ser Pro Ala Ala Ser Glu Asp Phe
        195                 200                 205

Thr Tyr Arg Pro Gly Asp Pro Val Phe Ser Phe Pro Ser Leu Pro Lys
    210                 215                 220

Asp Leu Leu His Thr Thr Pro Cys Phe Ile Pro Tyr His
225                 230                 235

<210> SEQ ID NO 36
<211> LENGTH: 244
<212> TYPE: PRT
<213> ORGANISM: Mus musculus

<400> SEQUENCE: 36

Met Pro Ala Pro Leu Glu Thr Cys Ile Ser Asp Leu Asp Cys Ser Ser
1               5                   10                  15

Ser Asn Ser Ser Ser Asp Leu Ser Ser Phe Leu Thr Asp Glu Glu Asp
                20                  25                  30

Cys Ala Arg Leu Gln Pro Leu Ala Ser Thr Ser Gly Leu Ser Val Pro
            35                  40                  45

Ala Arg Arg Ser Ala Pro Ala Leu Ser Gly Ala Ser Asn Val Pro Gly
```

-continued

```
                50                  55                  60
Ala Gln Asp Glu Glu Gln Glu Arg Arg Arg Arg Gly Arg Ala Arg
 65                  70                  75                  80

Val Arg Ser Glu Ala Leu Leu His Ser Leu Arg Arg Ser Arg Arg Val
                 85                  90                  95

Lys Ala Asn Asp Arg Glu Arg Asn Arg Met His Asn Leu Asn Ala Ala
                100                 105                 110

Leu Asp Ala Leu Arg Ser Val Leu Pro Ser Phe Pro Asp Asp Thr Lys
                115                 120                 125

Leu Thr Lys Ile Glu Thr Leu Arg Phe Ala Tyr Asn Tyr Ile Trp Ala
130                 135                 140

Leu Ala Glu Thr Leu Arg Leu Ala Asp Gln Gly Leu Pro Gly Gly Ser
145                 150                 155                 160

Ala Arg Glu Arg Leu Leu Pro Pro Gln Cys Val Pro Cys Leu Pro Gly
                165                 170                 175

Pro Pro Ser Pro Ala Ser Asp Thr Glu Ser Trp Gly Ser Gly Ala Ala
                180                 185                 190

Ala Ser Pro Cys Ala Thr Val Ala Ser Pro Leu Ser Asp Pro Ser Ser
                195                 200                 205

Pro Ser Ala Ser Glu Asp Phe Thr Tyr Gly Pro Gly Asp Pro Leu Phe
                210                 215                 220

Ser Phe Pro Gly Leu Pro Lys Asp Leu Leu His Thr Thr Pro Cys Phe
225                 230                 235                 240

Ile Pro Tyr His
```

```
<210> SEQ ID NO 37
<211> LENGTH: 214
<212> TYPE: PRT
<213> ORGANISM: Mus musculus

<400> SEQUENCE: 37

Met Ala Pro His Pro Leu Asp Ala Leu Thr Ile Gln Val Ser Pro Glu
 1               5                  10                  15

Thr Gln Gln Pro Phe Pro Gly Ala Ser Asp His Glu Val Leu Ser Ser
                20                  25                  30

Asn Ser Thr Pro Pro Ser Pro Thr Leu Ile Pro Arg Asp Cys Ser Glu
             35                  40                  45

Ala Glu Val Gly Asp Cys Arg Gly Thr Ser Arg Lys Leu Arg Ala Arg
 50                  55                  60

Arg Gly Gly Arg Asn Arg Pro Lys Ser Glu Leu Ala Leu Ser Lys Gln
 65                  70                  75                  80

Arg Arg Ser Arg Arg Lys Lys Ala Asn Asp Arg Glu Arg Asn Arg Met
                 85                  90                  95

His Asn Leu Asn Ser Ala Leu Asp Ala Leu Arg Gly Val Leu Pro Thr
                100                 105                 110

Phe Pro Asp Asp Ala Lys Leu Thr Lys Ile Glu Thr Leu Arg Phe Ala
                115                 120                 125

His Asn Tyr Ile Trp Ala Leu Thr Gln Thr Leu Arg Ile Ala Asp His
                130                 135                 140

Ser Phe Tyr Gly Pro Glu Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
```

-continued

```
               180                 185                 190
Gly Leu Gln Val Pro Ser Ser Pro Ser Tyr Leu Leu Pro Gly Ala Leu
            195                 200                 205
Val Phe Ser Asp Phe Leu
            210

<210> SEQ ID NO 38
<211> LENGTH: 214
<212> TYPE: PRT
<213> ORGANISM: Rattus norvegicus

<400> SEQUENCE: 38

Met Ala Pro His Pro Leu Asp Ala Pro Thr Ile Gln Val Ser Gln Glu
1               5                   10                  15
Thr Gln Gln Pro Phe Pro Gly Ala Ser Asp His Glu Val Leu Ser Ser
            20                  25                  30
Asn Ser Thr Pro Pro Ser Pro Thr Leu Val Pro Arg Asp Cys Ser Glu
        35                  40                  45
Ala Glu Ala Gly Asp Cys Arg Gly Thr Ser Arg Lys Leu Arg Ala Arg
    50                  55                  60
Arg Gly Gly Arg Asn Arg Pro Lys Ser Glu Leu Ala Leu Ser Lys Gln
65                  70                  75                  80
Arg Arg Ser Arg Arg Lys Lys Ala Asn Asp Arg Glu Arg Asn Arg Met
                85                  90                  95
His Asn Leu Asn Ser Ala Leu Asp Ala Leu Arg Gly Val Leu Pro Thr
            100                 105                 110
Phe Pro Asp Asp Ala Lys Leu Thr Lys Ile Glu Thr Leu Arg Phe Ala
        115                 120                 125
His Asn Tyr Ile Trp Ala Leu Thr Gln Thr Leu Arg Ile Ala Asp His
    130                 135                 140
Ser Phe Tyr Gly Pro Glu Pro Pro Val Pro Cys Gly Glu Leu Gly Ser
145                 150                 155                 160
Pro Gly Gly Gly Ser Ser Gly Asp Trp Gly Ser Ile Tyr Ser Pro Val
                165                 170                 175
Ser Gln Ala Gly Ser Leu Ser Pro Thr Ala Ser Leu Glu Glu Phe Pro
            180                 185                 190
Gly Leu Gln Val Pro Ser Ser Pro Ser Cys Leu Leu Pro Gly Thr Leu
        195                 200                 205
Val Phe Ser Asp Phe Leu
    210

<210> SEQ ID NO 39
<211> LENGTH: 214
<212> TYPE: PRT
<213> ORGANISM: Homo sapiens

<400> SEQUENCE: 39

Met Thr Pro Gln Pro Ser Gly Ala Pro Thr Val Gln Val Thr Arg Glu
1               5                   10                  15
Thr Glu Arg Ser Phe Pro Arg Ala Ser Glu Asp Glu Val Thr Cys Pro
            20                  25                  30
Thr Ser Ala Pro Pro Ser Pro Thr Arg Thr Pro Gly Asn Cys Ala Glu
        35                  40                  45
Ala Glu Glu Gly Gly Cys Arg Gly Ala Pro Arg Lys Leu Arg Ala Arg
    50                  55                  60
Arg Gly Gly Arg Ser Arg Pro Lys Ser Glu Leu Ala Leu Ser Lys Gln
```

-continued

```
                65                  70                  75                  80
Arg Arg Ser Arg Arg Lys Lys Ala Asn Asp Arg Glu Arg Asn Arg Met
                    85                  90                  95

His Asp Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
            115                 120                 125

His Asn Tyr Ile Trp Ala Leu Thr Gln Thr Leu Arg Ile Ala Asp His
            130                 135                 140

Ser Leu Tyr Ala Leu Glu Pro Ala Pro His Cys Gly Glu Leu Gly
145                 150                 155                 160

Ser Pro Gly Gly Pro Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
                180                 185                 190

Gly Leu Leu Gly Ala Thr Ser Ser Ala Cys Leu Ser Pro Gly Ser Leu
                195                 200                 205

Ala Phe Ser Asp Phe Leu
            210
```

<210> SEQ ID NO 40
<211> LENGTH: 263
<212> TYPE: PRT
<213> ORGANISM: Mus musculus

<400> SEQUENCE: 40

```
Met Phe Val Lys Ser Glu Thr Leu Glu Leu Lys Glu Glu Glu Val
1               5                   10                  15

Leu Met Leu Leu Gly Ser Ala Ser Pro Ala Ser Ala Thr Leu Thr Pro
                20                  25                  30

Met Ser Ser Ala Asp Glu Glu Asp Glu Glu Leu Arg Arg Pro
            35                  40                  45

Gly Ser Ala Arg Gly Gln Arg Gly Ala Glu Ala Glu Gln Gly Val Gln
    50                  55                  60

Gly Ser Pro Ala Ser Gly Ala Gly Cys Arg Pro Gly Arg Leu Leu
65                  70                  75                  80

Gly Leu Met His Glu Cys Lys Arg Arg Pro Ser Arg Ser Arg Ala Val
                85                  90                  95

Ser Arg Gly Ala Lys Thr Ala Glu Thr Val Gln Arg Ile Lys Lys Thr
                100                 105                 110

Arg Arg Leu Lys Ala Asn Asn Arg Glu Arg Asn Arg Met His Asn Leu
                115                 120                 125

Asn Ala Ala Leu Asp Ala Leu Arg Glu Val Leu Pro Thr Phe Pro Glu
            130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Ala Gly
                165                 170                 175

Ala Gly Gly Leu Gln Gly Ala Leu Phe Thr Glu Ala Val Leu Leu Ser
                180                 185                 190

Pro Gly Ala Ala Leu Gly Ala Ser Gly Asp Ser Pro Ser Pro Ser
                195                 200                 205

Ser Trp Ser Cys Thr Asn Ser Pro Ala Ser Ser Asn Ser Thr Ser
    210                 215                 220
```

```
                                    -continued
Pro Tyr Ser Cys Thr Leu Ser Pro Ala Ser Pro Gly Ser Asp Val Asp
225                 230             235             240

Tyr Trp Gln Pro Pro Pro Glu Lys His Arg Tyr Ala Pro His Leu
            245             250             255

Pro Leu Ala Arg Asp Cys Ile
            260
```

POLYPEPTIDES OF THE "BASIC HELIX-LOOP-HELIX" BHLH FAMILY, CORRESPONDING NUCLEIC ACID SEQUENCES

RELATED APPLICATIONS

This application is a Continuation-in-part of application Ser. No. 09/331,356 filed Jul. 12, 1999, now abandoned, which is a 35 U.S.C. §371 application of PCT/FR97/02368 filed Dec. 19, 1997. This application claims the benefit of foreign priority under 35 U.S.C. §119(a) to application FR96/15651 filed in France on Dec. 19, 1996.

FIELD OF THE INVENTION

The present invention relates to new bHLH-type polypeptides and to their corresponding coding nucleic acids. It also relates to expression vectors integrating said nucleic acids and to the use of these nucleic acids, vectors, or polypeptides for therapeutic purposes.

BACKGROUND OF THE INVENTION

The embryonic neuronal tube is at the outset composed of an undifferentiated neuroepithelium over its entire length. The cells then differentiate, depending on their positions on the anterior/posterior, dorsal/ventral and medium/lateral axes thereby generating various neuronal structures. This differentiation is in part controlled by genetic factors that subdivide the neuronal tube into several histogenic regions. It is now known that numerous transcriptional factors and, more particularly, products encoded by the so-called bHLH "Basic Helix Loop Helix" genes (Caudy et al., 1988, Cell, 55, 1061–67) are involved in this differentiation phenomenon. The proteins of this family have highly conserved amino acid units and more particularly a basic domain followed by Helix 1 and Helix 2. The latter two units are separated by a loop of variable size. In vertebrates, certain products of these bHLH genes participate in the various stages of neurogenesis during neuronal determination and differentiation. By way of representatives of these proteins, there may be mentioned in particular the Math-1 (Akazawa et al., 1995, J. Bol. Chem., 279,8730–38), Mash-1 (Johnson et al., 1990, 346, 858–61), and NeuroD (Lee et al., 1995, Sciences, 268, 836–44) proteins. Evidently, other proteins comprising this bHLH domain are involved in neuronal development at the level of other sites and at variable times. The identification of new bHLH-type proteins would be particularly valuable for increasing our understanding of neurogenesis and therefore be advantageous from the therapeutic point of view.

Members of the basic helix loop helix (bHLH) transcription factor family play a key role in a wide variety of cell fate determination and specification processes. These processes are as diverse as cardial muscle development[1], skeletal development[2], mesodermal cell determination[3], dermal cell differentiation[4] and more particularly, myogenesis[5] and neurogenesis[6].

Our understanding of the molecular basis of vertebrate nervous system development has benefitted from the identification of bHLH factors analogous to those regulating neurogenesis in *Drosophila*. In the fly, proneural bHLH genes, such as the four genes of the achaete-scute complex (AS-C) and the atonal gene are required for the fate determination of neuronal precursors within the ectoderm[6,7]. The expression of proneural genes in *Drosophila* is restricted to the neural precursor cells by lateral inhibition mediated by the Notch signaling pathway[8,9]. The search for vertebrate homologs of the *Drosophila* proneural genes has led to the identification of numerous genes encoding bHLH proteins. The AS-C homolog Mash1, the atonal homolog Math1 and the most recently identified genes of the neurogenin (ngn) family, including ngn1/Math4C, ngn2/Math4A and ngn3/Math4B/Relax have temporal and spatial expression patterns consistent with a function in neuronal determination[10]. The three neurogenin genes encode basic helix loop helix transcription factors. Functional analysis of these murine genes has shown that they play a key role in the determination of neuronal cell fate. In contrast, several other genes of the NeuroD family, including NeuroD/Beta2, Math2/Nex1, Math3 are more likely to be involved in differentiation than determination[10]. Functional analysis of these vertebrate genes has clearly suggested that the overall mechanism controlling neurogenesis is conserved throughout evolution at the fate determination and specification levels. The precise role in the developing nervous system of the putative neuronal determination genes has been investigated by gain-of-function and loss-of-function studies. The overexpression in *Xenopus* or Zebrafish embryos of some of the latter genes converts non-neural ectoderm into neurons suggesting that these genes encode neuronal determination factors[11-14]. Analysis of null mutations of Mash1, ngn1 and ngn2 has demonstrated that these genes have true determination functions affecting the development of at least a subset of neuronal cells[15-17].

SUMMARY OF THE INVENTION

The subject of the present invention is precisely the isolation, sequencing and characterization of cDNAs encoding polypeptides that belong to a new family of bHLH-type proteins. It also describes recombinant DNAs incorporating these nucleic acids, vectors containing them, and their use for activating the expression of recombinant proteins.

Applicants have now identified polypeptides possessing a high homology with the bHLH proteins already identified, a homology that is limited to the bHLH domain. Indeed, unexpectedly, the regions bordering this bHLH domain share no amino acid sequence identity with those of other bHLH-type proteins.

Consequently, the first subject of the present invention is a bHLH-type polypeptide endowed with a transcriptional activity, characterized in that it shares amino acid sequence homology with the bHLH-type proteins only at the level of its bHLH domain.

More precisely, the present invention relates to a polypeptide possessing a transcriptional activity, characterized in that it comprises completely or partly an amino acid sequence of either one of SEQ ID NOs: 8 or 10, or a derivative thereof.

Preferably, it is a bHLH-type polypeptide comprising an amino acid sequence represented in either one of SEQ ID NOs: 8 or 10. In a preferred embodiment, the bHLH-type polypeptide comprises 214 amino acids (SEQ ID NO: 8), for which the expression of the corresponding mRNA is detected in rat embryo in the form of longitudinal bands. This protein is designated hereinafter by the name Relax for "Rat Embryonic Longitudinal Axis" and constitutes a polypeptide according to the invention.

Comparison of the amino acid sequence of Relax with those of already available proteins has made it possible to establish a sequence correlation essentially with the bHLH-type proteins. Moreover, this homology has been located only at the level of the bHLH domain. The bHLH domain of Relax thus shares respectively 68%, 57% and 40% homology with the bHLH domains of the NeuroD, Math-1 and Mash-1 proteins.

From tests of activity carried out with the Relax protein and more precisely discussed in the examples below, it is evident that this protein is capable of binding specifically to an E box sequence and that in cotransfection trials, it behaves like a transcriptional activator and that this activity is strictly dependent on the presence of an intact E box. All these observations demonstrate the membership of the claimed Relax protein of a new family of bHLH proteins.

In another preferred embodiment, the bHLH-type polypeptide comprises 214 amino acids (SEQ ID NO: 10), which is designated hereinafter as human neurogenin 3 (hngn3) and constitutes a polypeptide according to the invention.

The subject of the present invention is also a nucleic acid that encodes a bHLH-type polypeptide according to the invention.

More precisely, the present invention relates to a nucleic acid comprising a polynucleotide sequence, characterized in that it is represented completely or partly by SEQ ID NOs: 1 or 9, or a complementary polynucleotide sequence or derivative thereof.

The claimed nucleic acids may be complementary DNA (cDNA), genomic DNA (gDNA) or RNA fragments. They may be more particularly cDNA or gDNA.

More preferably, it is a nucleic acid comprising a polynucleotide sequence of either one of SEQ ID NOs: 1 or 9, or of a complementary polynucleotide sequence thereof.

The present invention is also intended to cover corresponding anti-sense nucleic acids whose expression makes it possible to control the transcription of cellular mRNAs. Such nucleic acids may comprise all or part of a nucleic acid polynucleotide sequence according to the invention, transcribed in the reverse orientation. They are complementary or significantly complementary to the polynucleotide sequence of a nucleic acid according to the invention, either in total or in part.

The subject of the present invention is also the use of the polypeptides of the invention to control and/or participate in the expression of genes. These transcriptional activators may be most particularly advantageous for targeting the expression of a protein at the level of the central nervous system.

The polypeptides of the invention may be obtained by expressing, in a cellular host, a nucleic acid as described above, incorporated or otherwise into a recombinant DNA, using the techniques known to persons skilled in the art, or by a combination of these techniques.

Thus, the invention relates to a method for the production of a polypeptide according to the invention, wherein said method comprises the steps of:
  a) inserting a nucleic acid encoding said polypeptide into an appropriate vector;
  b) culturing, in an appropriate culture medium, a previously transformed host cell or transfecting a host cell with the recombinant vector of step a);
  c) recovering the conditioned culture medium or lysing the host cell, for example by sonication or by osmotic shock;
  d) separating and purifying said polypeptide from said culture medium or alternatively from the cell lysates obtained in step c); and
  e) where appropriate, characterizing the recombinant polypeptide produced.

Preferably, the nucleic acids according to the invention form part of a vector useful for inducing in vivo, ex vivo and/or in vitro the expression of the claimed polypeptides. The vector used may be of various origins, provided that it is capable of transforming animal cells, preferably human nerve cells. In a preferred embodiment of the invention, a viral vector, which may be derived from adenoviruses, retroviruses, adeno-associated viruses (AAV), the herpesvirus, the cytomegalovirus (CMV), the vaccinia virus, and the like, is used.

The present invention therefore also relates to any recombinant virus comprising, inserted into its genome, a nucleic acid according to the invention. Preferably, the recombinant virus according to the invention is a replication defective virus.

It is particularly advantageous to use the nucleic sequences of the invention in a form incorporated into an adenovirus, an AAV or a recombinant retrovirus that is defective. According to a preferred embodiment, it is an adenovirus. The vector, nucleic acid or polypeptide of the invention can be in an isolated or purified form.

The subject of the present invention is also a pharmaceutical composition comprising at least one nucleic acid, vector or polypeptide according to the invention and a pharmaceutically compatible excipient.

It also relates to any use of a nucleic acid, recombinant vector, or polypeptide according to the invention for the manufacture or preparation of a pharmaceutical composition or medicament intended for the treatment of a disease, condition, or pathology affecting the nervous system.

The present invention also provides nucleotide probes and primers that hybridize with a nucleic acid sequence of a nucleic acid according to the invention. The nucleotide probes or primers according to the invention comprise at least 8 consecutive nucleotides of a nucleic acid comprising a polynucleotide sequence of either one of SEQ ID NOs: 1 or 9, or of a complementary polynucleotide sequence. Preferably, nucleotide probes or primers according to the invention will have a length of at least 10, 12, 15, 18, 20 to 25, 35, 40, 50, 70, 80, 100, 200, 500, 1000, or 1500 consecutive nucleotides of a nucleic acid according to the invention.

The present invention also relates to a method of amplifying a nucleic acid according to the invention contained in a sample, wherein said method comprises the steps of:
  a) bringing the sample in which the presence of the target nucleic acid is suspected into contact with a pair of nucleotide primers whose hybridization position is located respectively on the 5'side and on the 3'side of the region of the target nucleic acid whose amplification is sought, in the presence of the reagents necessary for the amplification reaction; and
  b) detecting the amplified nucleic acids.

The present invention also relates to a method of detecting the presence of a nucleic acid according to the invention in a sample, wherein said method comprises the steps of:
  1) bringing one or more nucleotide probes according to the invention into contact with the sample to be tested;
  2) detecting the complex which may have formed between the probe(s) and the nucleic acid present in the sample.

Another subject of the invention is a box or kit for amplifying all or part of a nucleic acid according to the invention, wherein said box or kit comprises:
  1) a pair of nucleotide primers in accordance with the invention, whose hybridization position is located respectively on the 5'side and 3'side of the target nucleic acid whose amplification is sought; and optionally, 2) reagents necessary for an amplification reaction.

The invention also relates to a box or kit for detecting the presence of a nucleic acid according to the invention in a sample, said box or kit comprising:

a) one or more nucleotide probes according to the invention; and b) where appropriate, reagents necessary for a hybridization reaction.

The present invention also relates to a method of screening for antagonists or agonists of the polypeptides according to the invention. Preferably, the method of screening for antagonists or agonists of the polypeptides according to the invention is directed toward identifying an antagonist or agonist of a polypeptide comprising an amino acid sequence of either one of SEQ ID NO: 8 or SEQ ID NO: 10.

In a specific embodiment, the present invention relates to a method of identifying a modulator, agonist, or antagonist of a polypeptide according to the invention in a sample comprising a) obtaining a cell, for example a cell line, that, either naturally or after transfecting the cell with a nucleic acid encoding a polypeptide according to the invention, expresses a polypeptide according to the invention, b) transfecting the cell with a nucleic acid encoding a marker gene, such as β-galactosidase (β-gal), c) incubating the cell of step b) with a test solution or sample comprising a potential modulator, agonist or antagonist, d) measuring the amount of β-galactosidase activity, and e) comparing the amount of β-galactosidase activity measured in step d) with an amount of β-galactosidase activity measured with a cell that has not been previously incubated in the presence of the candidate modulator, agonist, or antagonist compound for the polypeptide according to the invention.

The present invention also relates to an antibody directed against a polypeptide according to the invention. Preferably, the antibody of the invention is directed against a polypeptide comprising an amino acid sequence of either one of SEQ ID NO: 8 or SEQ ID NO: 10.

The present invention relates to a method of detecting the presence of a polypeptide of the invention in a sample comprising the polypeptide. The present invention also relates to a kit for detecting the presence of a polypeptide of the invention in a sample comprising the polypeptide.

The present invention relates to a method of detecting the presence of a nucleic acid according to the invention in a sample comprising the nucleic acid. The present invention also relates to a kit for detecting the presence of a nucleic acid according to the invention in a sample comprising the nucleic acid.

The present invention also relates to a composition comprising a nucleic acid encoding a polypeptide according to the invention, wherein the nucleic acid is placed under the control of appropriate regulatory elements.

Thus, the present invention also relates to a pharmaceutical composition comprising a nucleic acid, polypeptide, or recombinant vector according to the invention, combined with one or more physiologically compatible vehicles and/or excipients.

The invention relates to an isolated recombinant host cell comprising a nucleic acid of the invention.

According to another aspect, the invention also relates to an isolated recombinant host cell comprising a recombinant vector according to the invention. Therefore, the invention also relates to a recombinant host cell comprising a recombinant vector comprising a nucleic acid of the invention.

The present invention also relates to the use of isolated cells genetically modified ex vivo with a nucleic acid or recombinant vector according to the invention, or of isolated cells producing a recombinant vector, wherein the cells are implanted in the body, to allow a prolonged and effective expression in vivo of a biologically active polypeptide according to the invention.

Thus, the invention also relates to the use of a recombinant host cell according to the invention, comprising a nucleic acid encoding a polypeptide according to the invention for the manufacture or preparation of a pharmaceutical composition or medicament intended for the prevention of, or more particularly, for the treatment of subjects affected by a nervous system pathology, dysfunction, disorder or condition.

The invention relates to the use of a defective recombinant virus according to the invention for the preparation of a pharmaceutical composition intended for the treatment and/or for the prevention of a disorder or condition affecting the nervous system. Thus, the present invention also relates to a pharmaceutical composition comprising a defective recombinant virus according to the invention, combined with one or more physiologically compatible vehicles and/or excipients.

The present invention also relates to the use of recombinant host cells genetically modified ex vivo with a recombinant defective virus according to the invention, or of recombinant host cells producing such viruses, implanted in the body, allowing a prolonged and effective expression in vivo of a biologically active protein of the invention. A specific embodiment of the invention is an isolated mammalian cell infected with one or more defective recombinant viruses according to the invention.

Another subject of the invention relates to an implant comprising isolated mammalian cells infected with one or more defective recombinant viruses according to the invention or cells producing recombinant viruses, and an extracellular matrix. More particularly, in the implants of the invention, the extracellular matrix comprises a gelling compound and optionally, a support allowing the anchorage of the cells.

Finally, the invention extends, in addition, to any use of a polypeptide, nucleic acid, recombinant vector, recombinant virus, recombinant host cell, or implant according to the invention to prevent and/or treat a dysfunction, disease, condition, or pathology affecting the nervous system or to control, influence, and/or participate in the expression of a gene.

BRIEF DESCRIPTION OF THE DRAWINGS

FIG. 1: Nucleotide sequence (SEQ ID NO: 29) of and amino acid (SEQ ID NO: 30) sequence encoded by the cDNA CIG235. The various oligonucleotides used to isolate the complete cDNA are indicated on this sequence. The arrows indicate the 5' to 3' orientation of these oligonucleotides.

FIG. 2: Comparison of the amino acid sequences of the bHLH domain of Relax (SEQ ID NO: 31) with other proteins of the family, including Math-1 (SEQ ID NO: 32), Neurod (SEQ ID NO: 33), and Mash1 (SEQ ID NO: 34). The homologous amino acids are noted in black, and the amino acids of similar structure in grey.

FIG. 3: Sequence of the hngn3 gene (SEQ ID NO: 9). The hngn3 coding region is indicated by capital letters. The deduced amino acid sequence (SEQ ID NO: 39) is presented above the nucleotide sequence. Both nucleotide and amino acid numbers are indicated on the left. The 138 bp PCR product amplified from the basic and helix II domain is underlined. The black arrow marks the 5'end of the 3'-anchored PCR product whereas the gray arrow indicates the 3' end of the 5'-anchored PCR product. The intron sequence interrupting the 5' untranslated region is boxed in gray.

FIG. 4: The amino acids sequences encoded by hngn3 (SEQ ID NO: 39), ngn3 (SEQ ID NO: 37), relax (SEQ ID NO: 38), ngn1 (SEQ ID NO: 36), ngn2 (SEQ ID NO: 40), and neuroD3 (SEQ ID NO: 35) genes were aligned using the Clustal-X program. The identity between the amino acid residues is displayed in color according to Clustal-X program parameters. (*) indicates residues conserved in all sequences.

FIGS. 5a and 5b: Optimal alignments obtained with the Clustal-X program were subjected to phylogenetic analysis with distance methods (Neighbor-Joining). The resulting trees correspond to the alignment of the bHLH domains only (a) or of the entire amino acid sequences (b). Bootstrap values are indicated near each branch. (a) Five paralogous groups highlighted on the right were clearly identified. This result is supported by the bootstrap value boxed in gray. (b) The phylogenetic relationships within the neurogenin family define three paralogous groups. All known members of the neurogenin are represented in this tree. Gene names according to the original publications are indicated in capital letters. The species from which the genes were isolated are indicated as a lower case prefix. dm=*Drosophila melanogaster*; ce=*Caenorhabditis elegans*; dr=*Danio rerio*; xl=*Xenopus laevis*; gg=*Gallus gallus*; mm=*Mus musculus*; rn=*Rattus norvegicus*; hs=*Homo sapiens*. Genebank accession numbers are as follows: dmDA=J03148; dmT8=X52892; dm T5=M17120; dmT4=M17119; dmT3=X12549; ceLIN32=U15418; dmATONAL=L36646; drATH1=AF024536; ggCATH1=U61149; mmMATH1=D43694; hsHATH1=U61148; mmMath3=D85845; drNEUROD=AF036148; mmMATH2=D44480; mmNEUROD2=U58771; mmNEUROD=U28068; hsNEUROD=D82347; dmTAP=X95845; xlNGNR1A=U67778; mmNGN2=U76207; ggNGN2=AJ012659; drNGN1=AF017301; ggNGN1=AJ012660; mmNGN1=U67776; rnNGN1=U67777; hsNEUROD3=U63842; mmNGN3=U76208; rnRELAX=Y10619; hsHNGN3=AJ133776; mmTWIST=M63649; mmSCLERAXIS=S78079; mmPARAXIS=U18658; mmEHAND=S79216; mmDHAND=U40039.

DETAILED DESCRIPTION OF THE INVENTION

Definitions

Figure 6:
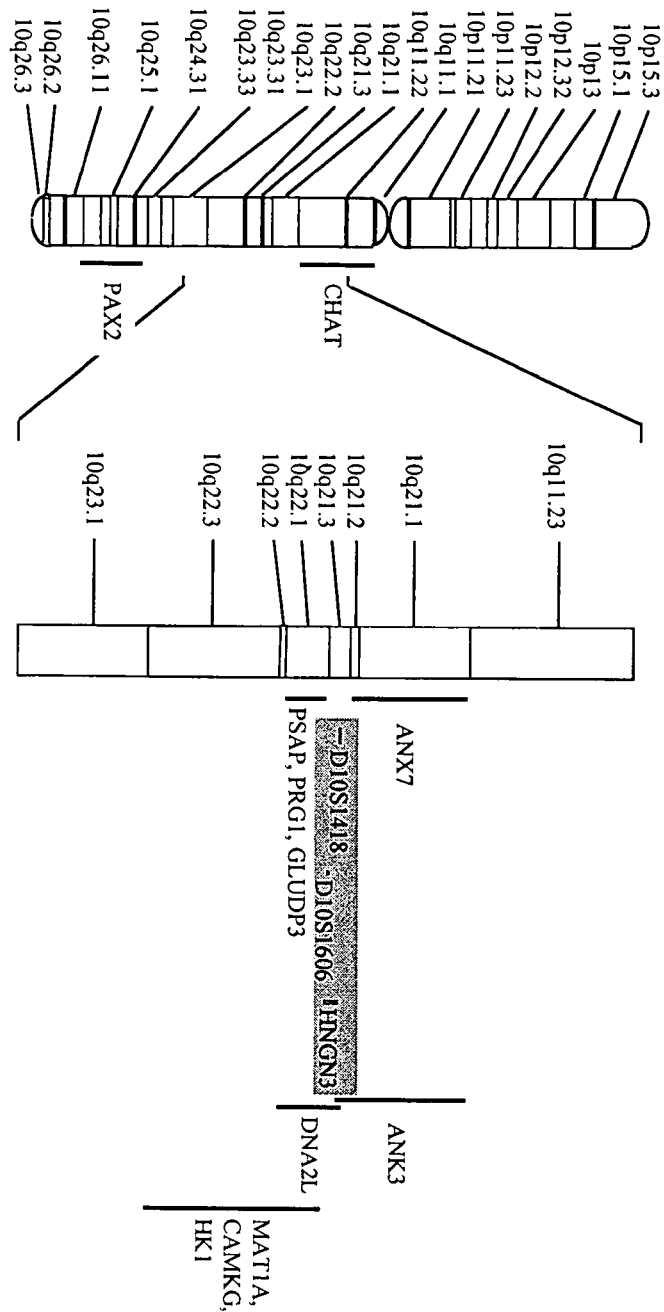
FIG. 6: The chromosomal location of hngn3 was determined by radiation hybrid mapping. Linkage analysis mapped hngn3 to 10q21.3, between the D10S1418 (GDB 684330) and D10S1603 (GDB 589266) markers (boxed in gray). A comprehensive map of chromosome 10 is shown on the left-hand side and a fine map of the region containing hngn3 is shown on the right-hand side. The maps were obtained using the mapview program of the genome database (GDB) package. The name of each gene and marker and their GDB accession numbers are as follow: D10S1418 (GDB 684330); D10S1603 (GDB 589266); CHAT=choline acetyltransferase (GDB 119775); PAX2=paired box homeotic gene 2 (GDB 138771), ANX7=annexin VII (GDB 369042); PSAP=prosaponin (GDB 120366); PRG1=platelet proteoglycan 1 protein core (GDB 120312); GLUDP3=glutamate dehydrogenase pseudogene 3 (GDB 137196); ANK3=ankyrin 3 (GDB 424503); DNA2L=DNA replication helicase (yeast homolog)-like (GDB 1313702); MAT1A=methionine adenosyltransferase I alpha (GDB 129077); CAMKG=CaM kinase II gamma (GDB 138469); HK1=hexokinase 1 (GDB 120044).

The following defined terms are used throughout the present specification, and should be helpful in understanding the scope and practice of the present invention.

In a specific embodiment, the term "about" or "approximately" means within 20%, preferably within 10%, and more preferably within 5% of a given value or range.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semisynthetic DNA.

A "gene" refers to an assembly of nucleotides that encode a polypeptide, and includes cDNA and genomic DNA nucleic acids.

A "recombinant DNA molecule" is a DNA molecule that has undergone a molecular biological manipulation.

A "vector" is any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. Viral vectors include retrovirus, adeno-associated virus, pox, baculovirus, vaccinia, herpes simplex, Epstein-Barr and adenovirus vectors, as set forth in greater detail below. Non-viral vectors include plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cloning vector" is a replicon, such as plasmid, phage or cosmid, to which another DNA segment may be attached so as to bring about the replication of the attached segment.

Cloning vectors may be capable of replication in one cell type, and expression in another ("shuttle vector").

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

For the purposes of the present invention, the term "derivative" designates any sequence differing from the sequence considered as a result of a degeneracy of the genetic code, obtained by one or more modifications of a genetic and/or chemical nature, as well as any sequence that hybridizes with these sequences or fragments thereof and whose product possesses the activity indicated.

Modification of a genetic and/or chemical nature is understood to mean any mutation, substitution, deletion, addition and/or modification of one or more residues. Such derivatives may be generated for various purposes, such as in particular that of enhancing its production levels that of increasing and/or modifying its activity, or that of conferring new pharmacokinetic and/or biological properties on it. Among the derivatives resulting from an addition, there may be mentioned, for example, the chimeric nucleic sequences comprising an additional heterologous part linked to one end, for example of the hybrid construct type consisting of a cDNA with which one or more introns would be associated.

Likewise, for the purposes of the invention, the claimed nucleic acids may comprise promoter, activating or regulatory sequences, and the like.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA: RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"High stringency hybridization conditions" for the purposes of the present invention will be understood to mean the following conditions:

1—Membrane Competition and Prehybridization:
  Mix: 40 µl salmon sperm DNA (10 mg/ml)+40 µl human placental DNA (10 mg/ml)
  Denature for 5 minutes at 96° C., then immerse the mixture in ice.
  Remove the 2×SSC and pour 4 ml of formamide mix in the hybridization tube containing the membranes.
  Add the mixture of the two denatured DNAs.
  Incubation at 42° C. for 5 to 6 hours, with rotation.

2—Labeled Probe Competition:
  Add to the labeled and purified probe 10 to 50 µl Cot I DNA, depending on the quantity of repeats.
  Denature for 7 to 10 minutes at 95° C.
  Incubate at 65° C. for 2 to 5 hours.

3—Hybridization:
  Remove the prehybridization mix.
  Mix 40 µl salmon sperm DNA+40 µl human placental DNA; denature for 5 min at 96° C., then immerse in ice.
  Add to the hybridization tube 4 ml of formamide mix, the mixture of the two DNAs and the denatured labeled probe/Cot I DNA.
  Incubate 15 to 20 hours at 42° C., with rotation.

4—Washes and Exposure:
  One wash at room temperature in 2×SSC, to rinse.
  Twice 5 minutes at room temperature 2×SSC and 0.1% SDS at 65° C.

Twice 15 minutes at 65° C. 1×SSC and 0.1% SDS at 65° C.

Envelope the membranes in clear plastic wrap and expose.

The hybridization conditions described above are adapted to hybridization, under high stringency conditions, of a molecule of nucleic acid of varying length from 20 nucleotides to several hundreds of nucleotides. It goes without saying that the hybridization conditions described above may be adjusted as a function of the length of the nucleic acid whose hybridization is sought or of the type of labeling chosen, according to techniques known to one skilled in the art. Suitable hybridization conditions may, for example, be adjusted according to the teaching contained in Hames and Higgins, 1985 (Nucleic acid hybridization: a practical approach, Hames and Higgins Ed., IRL Press, Oxford) and Ausubel et al., 1989 (Current Protocols in Molecular Biology, Green Publishing Associates and Wiley Interscience, N.Y.).

As used herein, the term "oligonucleotide" refers to a nucleic acid, generally of at least 18 nucleotides, that is hybridizable to a genomic DNA molecule, a cDNA molecule, or an mRNA molecule encoding a polypeptide of the invention. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid encoding a polypeptide of the invention. In another embodiment, oligonucleotides (one or both of which may be labeled) can be used as PCR primers, either for cloning full length or a fragment of a polypeptide of the invention, or to detect the presence of nucleic acids encoding a polypeptide of the invention. In a further embodiment, an oligonucleotide of the invention can form a triple helix with a DNA molecule of the invention. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA "coding sequence" is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

An "antisense nucleic acid" is a sequence of nucleotides that is complementary to the sense sequence. Antisense nucleic acids can be used to down regulate or block the expression of the polypeptide encoded by the sense strand. The present invention is also intended to cover corresponding anti-sense nucleic acids whose expression makes it possible to control the transcription of cellular mRNAs. Such nucleic acids may comprise all or part of a nucleic acid polynucleotide sequence according to the invention, transcribed in the reverse orientation. They are complementary or significantly complementary to the polynucleotide sequence of a nucleic acid according to the invention, either in total or in part.

Transcriptional and translational control sequences are DNA regulatory sequences, such as promoters, enhancers, terminators, and the like, that provide for the expression of a coding sequence in a host cell. In eukaryotic cells, polyadenylation signals are additional types of control sequences.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin which are responsible for expressing different proteins or even synthetic proteins (a heterologous region). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, promoters, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"Heterologous" DNA refers to DNA not naturally located in the cell, or in a chromosomal site of the cell. Preferably, the heterologous DNA includes a gene foreign to the cell.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A "polypeptide" is a polymeric compound comprised of covalently linked amino acid residues. Amino acids have the following general structure:

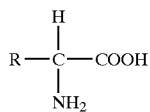

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide which plays a structural or functional role in a living cell.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant of the invention preferably comprises at least about 14 amino acids.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "heterologous protein" refers to a protein not naturally produced in the cell.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "derivative" is understood to mean, for the purposes of the present invention, the products comprising, for example, modifications at the level of the primary structure, such as deletions of one or more residues, substitutions of one or more residues, and/or modifications at the level of one or more residues. The number of residues affected by the modifications may be, for example, from 1, 2 or 3 to 10, 20, or 30 residues. The term derivative also comprises the molecules comprising additional internal or terminal parts, of a peptide nature or otherwise. They may be in particular active parts, markers, amino acids, such as methionine at position −1. The term derivative also comprises the molecules comprising modifications at the level of the tertiary structure (N-terminal end, and the like). The term derivative also comprises sequences homologous to the sequence considered, derived from other cellular sources, and in particular from cells of human origin, or from other organisms, and possessing activity of the same type or of substantially similar type. Such homologous sequences may be obtained by hybridization experiments. The hybridizations may be performed based on nucleic acid libraries, using, as probe, the native sequence or a fragment thereof, under conventional stringency conditions (Maniatis et al., General Molecular Biology Techniques), or preferably under high stringency conditions.

These derivatives may be generated for various purposes, such as in particular that of increasing the affinity of the peptide for its site(s) of interaction, that of enhancing its production levels, or that of conferring new pharmacokinetic and/or biological properties on it.

Preferably, the derivatives share at least one structural homology with a polypeptide according to the invention and more preferably at least at the level of the regions bordering the bHLH domain, and conserve its biological property of transcriptional activator. The derivatives may also offer new properties to the claimed polypeptides (labelling, and the like), or enhance their properties (stability, biological activity and the like).

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A gene encoding a polypeptide according to the invention, whether genomic DNA or cDNA, can be isolated from any source, particularly from a human cDNA or genomic library. General methods for obtaining such a gene are well known in the art, as described above (see, e.g., Sambrook et al., 1989, supra).

Accordingly, any animal cell potentially can serve as the nucleic acid source for the molecular cloning of a gene according to the invention. The DNA may be obtained by standard procedures known in the art from cloned DNA (e.g., a DNA "library"), and preferably is obtained from a cDNA library prepared from tissues with high level expression of the protein (e.g., heart, pancreas and skeletal muscle cDNA, since these are the cells that evidence high levels of expression of a polypeptide according to the invention), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Once the DNA fragments are generated, identification of the specific DNA fragment containing the desired gene of the invention may be accomplished in a number of ways. For example, DNA fragments may be screened by nucleic acid hybridization to a labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. As noted above, the greater the degree of homology, the more stringent hybridization conditions can be used. In a specific embodiment, Northern hybridization conditions are used to identify mRNA splicing variants of a gene according to the invention.

Further selection can be carried out on the basis of the properties of the gene, e.g., if the gene encodes a protein product having the isoelectric, electrophoretic, amino acid composition, or partial amino acid sequence of a polypeptide according to the invention as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for a polypeptide according to the invention. In a specific embodiment, the expressed protein is recognized by a polyclonal antibody that is generated against an epitope specific for human ngn3 peptide.

The present invention also relates to genes (e.g., cDNAs) encoding allelic variants, splicing variants, analogs, and derivatives of a polypeptide according to the invention, that have the same or homologous functional activity as a polypeptide according to the invention, and homologs thereof from other species. The production and use of derivatives and analogs related to polypeptides of the invention are within the scope of the present invention. In a specific embodiment, the derivative or analog is functionally active, i.e., capable of exhibiting one or more functional activities associated with a full-length, wild-type Relax or hngn3 polypeptide of the invention.

A derivative of a polypeptide according to the invention can be made by altering encoding nucleic acid sequences by substitutions, additions or deletions that provide for functionally equivalent molecules. Preferably, derivatives are made that have enhanced or increased functional activity relative to native Relax or hngn3 polypeptide.

Due to the degeneracy of nucleotide coding sequences, other DNA sequences which encode substantially the same amino acid sequence as a Relax gene or an hngn3 gene, including an amino acid sequence that contains a single amino acid variant, may be used in the practice of the present invention. These include but are not limited to allelic genes, homologous genes from other species, and nucleotide sequences comprising all or portions of a gene according to the invention that is altered by the substitution of different codons that encode the same amino acid residue within the sequence, thus producing a silent change. Likewise, the derivatives of the invention include, but are not limited to, those containing, as a primary amino acid sequence, all or part of the amino acid sequence of a Relax polypeptide or an hngn3 polypeptide including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding derivatives and analogs of the invention can be produced by various methods known in the art. The manipulations that result in their production can occur at the gene or protein level. For example, a cloned gene sequence according to the invention can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a polypeptide according to the invention, care should be taken to ensure that the modified gene remains within the same translational reading frame as the wild-type gene, uninterrupted by translational stop signals, in the gene region where the desired activity is encoded.

Additionally, the nucleic acid sequence encoding a polypeptide according to the invention can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *Escherichia coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector that has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. Coli*, and purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2µ plasmid.

Nucleic Acids Encoding Relax and hngn3 Polypeptides

The present invention relates to nucleic acids encoding novel basic helix-loop-helix polypeptides, Relax and hngn3. Thus, a first subject of the invention is a nucleic acid comprising a polynucleotide sequence of a) SEQ ID NO: 1, or of a complementary polynucleotide sequence, or b) SEQ ID NO: 9, or of a complementary polynucleotide sequence.

The invention also relates to a nucleic acid comprising at least 8 consecutive nucleotides of a polynucleotide sequence of a) SEQ ID NO: 1, or of a complementary polynucleotide sequence, or b) SEQ ID NO: 9, or of a complementary polynucleotide sequence.

Preferably, a nucleic acid according to the invention comprises at least 10, 12, 15, 18, 20 to 25, 35, 40, 50, 70, 80, 100, 200, or 500 consecutive nucleotides of a polynucleotide sequence of a) SEQ ID NO: 1, or of a complementary polynucleotide sequence, or b) SEQ ID NO: 9, or of a complementary polynucleotide sequence.

The invention also relates to a nucleic acid having at least 80% nucleotide identity with a nucleic acid comprising a polynucleotide sequence of a) SEQ ID NO: 1, or of a complementary polynucleotide sequence, or b) SEQ ID NO: 9, or of a complementary polynucleotide sequence.

The invention also relates to a nucleic acid having at least 85%, preferably 90%, more preferably 95% and still more preferably 98% nucleotide identity with a nucleic acid comprising a polynucleotide sequence of a) SEQ ID NO: 1, or of a complementary polynucleotide sequence, or b) SEQ ID NO: 9, or of a complementary polynucleotide sequence.

The invention also relates to a nucleic acid hybridizing, under high stringency conditions, with a polynucleotide sequence of a) SEQ ID NO: 1, or of a complementary polynucleotide sequence, or b) SEQ ID NO: 9, or of a complementary polynucleotide sequence.

The invention also relates to nucleic acids, particularly cDNA molecules, which encode the full length rat Relax or human ngn3 proteins. The present invention also relates to a cDNA molecule that encodes the novel full length rat Relax or human ngn3 proteins. Thus, the invention relates to a nucleic acid comprising a polynucleotide sequence of a) SEQ ID NO: 1, or of a complementary polynucleotide sequence, or b) SEQ ID NO: 9, or of a complementary polynucleotide sequence.

The invention also relates to a nucleic acid comprising a polynucleotide sequence as depicted in a) SEQ ID NO: 1, or of a complementary polynucleotide sequence, or b) SEQ ID NO: 9, or of a complementary polynucleotide sequence.

According to the invention, a nucleic acid comprising a polynucleotide sequence of SEQ ID NO: 1 encodes a full length rat Relax polypeptide of 214 amino acids comprising the amino acid sequence of SEQ ID NO: 8.

According to the invention, a nucleic acid comprising a polynucleotide sequence of SEQ ID NO: 9 encodes a full length human hngn3 polypeptide of 214 amino acids comprising the amino acid sequence of SEQ ID NO: 10.

Relax and hngn3 Polypeptides According to the Invention

The present invention also relates to rat Relax or human ngn3 (hngn3) polypeptides according to the invention.

Thus, the present invention relates to a nucleic acid that encodes a polypeptide comprising an amino acid sequence of either one of SEQ ID NOs: 8 or 10.

The invention also relates to a polypeptide comprising an amino acid sequence as depicted in either one of SEQ ID NOs: 8 or 10.

The invention also relates to a polypeptide comprising an amino acid sequence having at least 80% amino acid identity with a polypeptide comprising an amino acid sequence of either one of SEQ ID NOs: 8 or 10.

The invention also relates to a polypeptide having at least 85%, preferably 90%, more preferably 95% and still more preferably 98% amino acid identity with a polypeptide comprising an amino acid sequence of either one of SEQ ID NOs: 8 or 10.

Preferably, a polypeptide according to the invention will have a length of 15, 18 or 20 to 25, 35, 40, 50, 70, 80, 100 or 200 consecutive amino acids of a polypeptide according to the invention, in particular a polypeptide comprising an amino acid sequence of either one of SEQ ID NOs: 8 or 10.

Alternatively, a polypeptide according to the invention will comprise a fragment having a length of 15, 18, 20, 25, 35, 40, 50, 100 or 200 consecutive amino acids of a polypeptide according to the invention, more particularly of a polypeptide comprising an amino acid sequence of either one of SEQ ID NOs: 8 or 10.

Expression of Polypeptides of the Invention and Methods of Producing Polypeptides of the Invention The invention relates to a method for the production of a polypeptide comprising an amino acid sequence of either one of SEQ ID NOs: 8 or 10, or of a polypeptide or a variant thereof, wherein said method comprises the steps of:

a) inserting a nucleic acid encoding said polypeptide into an appropriate vector;

b) culturing, in an appropriate culture medium, a previously transformed host cell or transfecting a host cell with the recombinant vector of step a);

c) recovering the conditioned culture medium or lysing the host cell, for example by sonication or by osmotic shock;

d) separating and purifying said polypeptide from said culture medium or alternatively from the cell lysates obtained in step c); and e) where appropriate, characterizing the recombinant polypeptide produced.

A specific embodiment of the invention relates to a method for producing a polypeptide comprising an amino acid sequence of either one of SEQ ID NOs: 8 or 10.

A polypeptide termed "homologous" to a polypeptide having an amino acid sequence comprising either one of SEQ ID NOs: 8 or 10 also forms part of the invention. Such a homologous polypeptide comprises an amino acid sequence possessing one or more substitutions of an amino acid by an equivalent amino acid, relative to either one of SEQ ID NOs: 8 or 10, respectively.

The polypeptides according to the invention may be characterized by binding to an immunoaffinity chromatography column on which the antibodies directed against this polypeptide or against a fragment or a variant thereof have been previously immobilized.

According to another aspect, a recombinant polypeptide according to the invention may be purified by passing it over an appropriate series of chromatography columns, according to methods known to persons skilled in the art and described for example in Ausubel et al. (1989).

A polypeptide according to the invention may also be prepared by conventional chemical synthesis techniques either in homogeneous solution or in solid phase. By way of illustration, a polypeptide according to the invention may be prepared by the technique either in homogeneous solution described by Houben Weyl, 1974 (In: Meuthode der Organischen Chemie, E. Wunsch Ed., 15-I:15-II) or the solid phase synthesis technique described by Merrifield, 1965 (Nature, 207(996):522–523 and Science, 150(693):178–185).

An "equivalent amino acid" according to the present invention will be understood to mean for example replacement of a residue in the L form by a residue in the D form or the replacement of a glutamic acid (E) by a pyro-glutamic acid according to techniques well known to persons skilled in the art. By way of illustration, the synthesis of peptide containing at least one residue in the D form is described by Koch, 1977 (Biochem. Biophys. Res. Commun., 74:488–491). According to another aspect, two amino acids belonging to the same class, that is to say two uncharged polar, nonpolar, basic or acidic amino acids, are also considered as equivalent amino acids.

Polypeptides comprising at least one nonpeptide bond such as a retro-inverse bond (NHCO), a carba bond ($CH_2CH_2$) or a ketomethylene bond (CO—$CH_2$) also form part of the invention.

Preferably, the polypeptides according to the invention comprising one or more additions, deletions, substitutions of at least one amino acid will retain their capacity to be recognized by antibodies directed against the nonmodified polypeptides.

The nucleotide sequence coding for a polypeptide according to the invention, or antigenic fragment, derivative or analog thereof, or a functionally active derivative, including a chimeric protein, thereof, can be inserted into an appropriate expression vector, i.e., a vector that contains the necessary elements for the transcription and translation of the inserted protein-coding sequence. Such elements are termed herein a "promoter." Thus, the nucleic acid of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a polypeptide according to the invention and/or its flanking regions. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant polypeptide of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding a polypeptide according to the invention is cultured in an appropriate cell culture medium under conditions that provide for expression of the polypeptide by the cell. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

A nucleic acid encoding a polypeptide according to the invention may be operably linked and controlled by any regulatory region, i.e., promoter/enhancer element known in the art, but these regulatory elements must be functional in the host target tumor selected for expression. The regulatory regions may comprise a promoter region for functional transcription in the host cell, as well as a region situated 3' of the gene of interest, and which specifies a signal for termination of transcription and a polyadenylation site. All these elements constitute an expression cassette.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell that it is desired to infect. Likewise, it may be promoter sequences derived from the genome of a virus, such as adenovirus (E1A and MLP), cytomegalovirus (CMV), or Rous Sarcoma Virus (RSV). In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted.

Some promoters useful for practice of this invention are ubiquitous promoters (e.g., HPRT, vimentin, actin, tubulin), intermediate filament promoters (e.g., desmin, neurofilaments, keratin, GFAP), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, cytomegalovirus (CMV) immediate-early, retroviral LTR, metallothionein, SV-40, adenovirus E1a, and adenovirus major late (MLP) promoters. Tetracycline-regulated transcriptional modulators and CMV promoters are described in WO 96/01313, U.S. Pat. Nos. 5,168,062 and 5,385,839, the contents of which are incorporated herein by reference.

More specifically, expression of a polypeptide according to the invention may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other flingi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Omitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding a polypeptide of the invention can be identified by five general approaches: (a) PCR amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a polypeptide according to the invention is inserted within the "selection marker" gene sequence of the vector, recombinants containing the nucleic acid insert can be identified by the absence of the gene function. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoRI, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C [three different reading frames, with BamH1, BglII, PstI, NcoI, and HindIII cloning site, an N-terminal peptide for ProBond purification, and blue/white recombinant screening of plaques; Invitrogen (220)] can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive Rous Sarcoma Virus Long Terminal Repeat (RSV-LTR) promoter, hygromycin selectable marker; Invitrogen), pCEP4 (BamH1, SfiI, XhoI, NotI, NheI, HindIII, NheI, PvuII, and KpnI cloning site, constitutive human cytomegalovirus (hCMV) immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express a polypeptide according to the invention. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. Expression in yeast can produce a biologically active product. Expression in eukaryotic cells can increase the likelihood of "native" folding. Moreover, expression in mammalian cells can provide a tool for reconstituting, or constituting, activity of a polypeptide according to the invention. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Antibodies of the Invention

A polypeptide according to the invention produced recombinantly or by chemical synthesis, and fragments or other derivatives or analogs thereof, including fusion proteins, may be used as an antigen or immunogen to generate antibodies. Preferably, the antibodies specifically bind to Relax or ngn3 polypeptide according to the invention. More preferably, the antibodies specifically bind human ngn3, but do not bind other forms of ngn3.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Such antibodies include but are not limited to polyclonal, monoclonal, chimeric, single chain, Fab fragments, and an Fab expression library. The antibodies of the invention may be cross reactive, e.g., they may recognize Relax or ngn3 from different species. Polyclonal antibodies have greater likelihood of cross reactivity. Alternatively, an antibody of the invention may be specific for a single form of ngn3, such as human ngn3. Preferably, such an antibody is specific for human ngn3.

Various procedures known in the art may be used for the production of polyclonal antibodies. For the production of antibody, various host animals can be immunized by injection with a polypeptide according to the invention, or a derivative (e.g., fragment or fusion protein) thereof, including but not limited to rabbits, mice, rats, sheep, goats, etc. In one embodiment, the polypeptide according to the invention or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a polypeptide according to the invention, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals [International Patent Publication No. WO 89/12690, published 28 Dec. 1989]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for a polypeptide according to the invention together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain Fv (scFv) antibodies [U.S. Pat. Nos. 5,476,786 and 5,132,405 to Huston; U.S. Pat. No. 4,946,778] can be adapted to produce polypeptide-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a polypeptide according to the invention, or its derivatives, or analogs.

Antibody fragments that contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies that recognize a specific epitope of a polypeptide according to the invention, one may assay generated hybridomas for a product that binds to a polypeptide fragment conmprising such an epitope. For selection of an antibody specific to a polypeptide of the invention from a particular species of animal, one can select on the basis of positive binding with the polypeptide expressed by or isolated from cells of that species of animal.

The foregoing antibodies can be used in methods known in the art relating to the localization and activity of a polypeptide of the invention, e.g., for Western blotting, imaging the polypeptide in situ, measuring levels thereof in appropriate physiological samples, etc., using any of the detection techniques mentioned above or known in the art.

In a specific embodiment, antibodies that agonize or antagonize the activity of a Relax or hngn3 polypeptide can be generated. Such antibodies can be tested using the assays for identifying ligands. In particular, such antibodies can be scFv antibodies expressed intracellularly.

The present invention relates to an antibody directed against a polypeptide comprising an amino acid sequence of
1) either one of SEQ ID NOs: 8 or 10,
2) a polypeptide fragment or variant of a polypeptide comprising an amino acid sequence of either one of SEQ ID NOs: 8 or 10, or
3) a polypeptide termed "homologous" to a polypeptide comprising either one of SEQ ID NOs: 8 or 10, as produced in the trioma technique or the hybridoma technique described by Kozbor et al. also forms part of the invention.

The invention also relates to single-chain Fv antibody fragments (ScFv) as described in U.S. Pat. No. 4,946,778 or by Martineau et al. (J Mol Biol, 280(1):117–127, 1998).

The antibodies according to the invention also comprise antibody fragments obtained with the aid of phage libraries (Martineau et al., Ibid.) or humanized antibodies [Reimann et al. (AIDS Res Hum Retroviruses, 13(11):933–943, 1997) and Leger et al. (Hum Antibodies, 8(1):3–16, 1997)].

The antibody preparations according to the invention are useful in immunological detection tests intended for the identification of the presence and/or of the quantity of antigens present in a sample.

An antibody according to the invention may comprise, in addition, a detectable marker that is isotopic or nonisotopic, for example fluorescent, or may be coupled to a molecule such as biotin, according to techniques well known to persons skilled in the art.

Thus, another subject of the invention is a method of detecting the presence of a polypeptide according to the invention in a sample, said method comprising the steps of:
a) bringing the sample to be tested into contact with an antibody directed against
1) a polypeptide comprising an amino acid sequence of either one of SEQ ID NOs: 8 or 10,
2) a polypeptide fragment or variant of a polypeptide comprising an amino acid sequence of either one of SEQ ID NOs: 8 or 10, or
3) a polypeptide termed "homologous" to a polypeptide comprising either one of SEQ ID NOs: 8 or 10, and
b) detecting the antigen/antibody complex formed.

The invention also relates to a box or kit for diagnosis or for detecting the presence of a polypeptide in accordance with the invention in a sample, said box comprising:
a) an antibody directed against
1) a polypeptide comprising an amino acid sequence of either one of SEQ ID NOs: 8 or 10,
2) a polypeptide fragment or variant of a polypeptide comprising an amino acid sequence of either one of SEQ ID NOs: 8 or 10, or
3) a polypeptide termed "homologous" to a polypeptide comprising either one of SEQ ID NOs: 8 or 10, and
b) a reagent allowing the detection of the antigen/antibody complex formed.

Gene Therapy and Transgenic Vectors

The invention also relates to a recombinant vector comprising a nucleic acid according to the invention. "Vector" for the purposes of the present invention will be understood to mean a circular or linear DNA or RNA molecule that is either in single-stranded or double-stranded form.

Preferably, such a recombinant vector will comprise a nucleic acid selected from the group consisting of
a) a nucleic acid comprising a polynucleotide sequence of either one of SEQ ID NOs: 1 or 9, or of a complementary polynucleotide sequence,
b) a nucleic acid comprising a polynucleotide sequence as depicted in either one of SEQ ID NOs: 1 or 9, or of a complementary polynucleotide sequence,
c) a nucleic acid having at least eight consecutive nucleotides of a nucleic acid comprising a polynucleotide sequence of 1) SEQ ID NO: 1, or of a complementary polynucleotide sequence, or 2) SEQ ID NO: 9, or of a complementary polynucleotide sequence,
d) a nucleic acid having at least 80% nucleotide identity with a nucleic acid comprising a polynucleotide sequence of either one of SEQ ID NOs: 1 or 9, or of a complementary polynucleotide sequence,
e) a nucleic acid having 85%, 90%, 95%, or 98% nucleotide identity with a nucleic acid comprising a polynucleotide sequence of either one of SEQ ID NOs: 1 or 9, or of a complementary polynucleotide sequence,
f) a nucleic acid hybridizing, under high stringency hybridization conditions, with a nucleic acid comprising a polynucleotide sequence of either one of SEQ ID NOs: 1 or 9, or of a complementary polynucleotide sequence, and
g) a nucleic acid encoding a polypeptide comprising an amino acid sequence of either one of SEQ ID NOs: 8 or 10.

According to a first embodiment, a recombinant vector according to the invention is used to amplify a nucleic acid inserted therein, following transformation or transfection of a desired cellular host.

According to a second embodiment, a recombinant vector according to the invention corresponds to an expression vector comprising, in addition to a nucleic acid in accordance with the invention, a regulatory signal or nucleotide sequence that directs or controls transcription and/or translation of the nucleic acid and its encoded mRNA.

According to a preferred embodiment, a recombinant vector according to the invention will comprise in particular the following components:

(1) an element or signal for regulating the expression of the nucleic acid to be inserted, such as a promoter and/or enhancer sequence;

(2) a nucleotide coding region comprised within the nucleic acid in accordance with the invention to be inserted into such a vector, said coding region being placed in phase with the regulatory element or signal described in (1); and (3) an appropriate nucleic acid for initiation and termination of transcription of the nucleotide coding region of the nucleic acid described in (2).

In addition, the recombinant vectors according to the invention may include one or more origins for replication in the cellular hosts in which their amplification or their expression is sought, markers or selectable markers.

The present invention also includes gene therapy by the administration to a patient of a nucleic acid encoding a polypeptide according to the invention. Preferably, the nucleic acid encodes a human ngn3 protein.

The nucleic acids of the invention, where appropriate incorporated in vectors, and the pharmaceutical compositions comprising them, may be used for the treatment of many pathologies or dysfunction. They may be used for the transfer and expression of genes in vivo in any type of tissue, especially the nervous system. The treatment can, moreover, be targeted in accordance with the pathology or dysfunction to be treated (transfer to a particular tissue can, in particular, be determined by the choice of a vector, and expression by the choice of a particular promoter). The nucleic acids or vectors of the invention are advantageously used for the production in humans or animals, in vivo and intracellularly, of proteins capable of acting specifically on various cell functions such as cell proliferation, cell differentiation, neurogenesis, and the like. The present invention thus makes it possible to treat specifically, locally and effectively cell dysfunctions at the origin of or resulting from different pathologies affecting neurogenesis.

As discussed above, a "vector" is any means for the transfer of a nucleic acid according to the invention into a host cell. Preferred vectors are viral vectors, such as retroviruses, herpes viruses, adenoviruses, and adeno-associated viruses. Thus, a gene encoding a polypeptide according to the invention or a fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Expression vectors of the invention can be used, as pointed out above, both to transfect cells for screening or biological testing of modulators of the polypeptides according to the invention, or for delivery of a gene or antisense gene according to the invention in vivo or ex vivo for gene therapy, e.g., to increase or decrease the level of activity of a polypeptide of the invention. A vector that expresses a scFv of the invention can also be introduced using the techniques discussed below.

Viral vectors commonly used for in vivo or ex vivo targeting and therapy procedures are DNA-based vectors and retroviral vectors. Methods for constructing and using viral vectors are known in the art [see, e.g., Miller and Rosman, *BioTechniques* 7:980–990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome that are necessary for encapsulating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Vectors derived from adenoviruses, retroviruses or AAVs incorporating heterologous nucleic acid sequences have been described in the literature [Akli et al., Nature Genetics 3 (1993) 224; Stratford-Perricaudet et al., Human Gene Therapy 1 (1990) 241; EP 185 573, Levrero et al., Gene 101 (1991) 195; Le Gal La Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088].

The present invention therefore also relates to any recombinant virus comprising, inserted into its genome, a nucleic acid according to the invention.

Defective viruses, which entirely or almost entirely lack viral genes, are preferred. The term "defective virus" designates a virus incapable of replicating in the target cell. Generally, the genome of the defective viruses used in the context of the present invention therefore lacks at least sequences necessary for the replication of the virus in the infected cell. These regions may be either removed (completely or partly), or made nonfunctional, or substituted by other sequences and in particular by the nucleic acid of the invention. Preferably, the defective virus conserves, nevertheless, the sequences of its genome that are necessary for the encapsidation of the viral particles. Defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., *Molec. Cell. Neurosci.* 2:320–330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626–630 (1992); see also Le Gal La Salle et al., Science 259:988–990 (1993)]; and a defective adeno-associated virus vector [Samulski et al., *J. Virol.* 61:3096–3101 (1987); Samulski et al., *J. Virol.* 63:3822–3828 (1989); Lebkowski et al., *Mol. Cell. Biol.* 8:3988–3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

Naturally, the invention contemplates delivery of a vector that will express a therapeutically effective amount of a polypeptide of the invention for gene therapy applications. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Adenovirus Vectors

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist, whose structure and properties vary somewhat. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin that can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example). Preferably, adenoviruses of human or canine or mixed origin are used in the context of the invention.

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1–L5. The viral gene considered can be made nonfunctional by any technique known to persons skilled in the art, and in particular by total suppression, by substitution or partial deletion or by addition of one or more bases in the gene(s) considered.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence of interest is inserted (see FR94 13355, the contents of which are incorporated herein by reference). According to another preferred embodiment, the exogenous nucleic acid sequence is inserted at the level of the deletion in the E1 region.

The replication defective recombinant viruses of the invention can be prepared by any technique known to the person skilled in the art (Levrero et al., Gene 101 (1991) 195, EP 185 573; Graham, EMBO J. 3 (1984) 2917). In particular, they can be prepared by homologous recombination between a defective adenovirus and a plasmid that carries, inter alia, the DNA sequence of interest. The homologous recombination occurs after co-transfection of the adenovirus and plasmid into an appropriate cell line. The cell line which is employed should preferably (i) be transformable by the said elements, and (ii) comprise the nucleic acid sequences that are able to complement the defective virus genome part, preferably in integrated form in order to avoid the risks of recombination. Examples of cell lines which may be used for the preparation of defective recombinant adenoviruses are the human embryonic kidney cell line 293 [Graham et al., J. Gen. Virol. 36 (1977) 59] which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-Associated Virus Vectors

The adeno-associated viruses (AAV) are DNA viruses of relatively small size that can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterised. It encompasses approximately 4700 bases and contains an inverted terminal repeat (ITR) region of approximately 145 bases at each end, which serves as an origin of replication for the virus. The remainder of the genome is divided into two essential regions which carry the encapsulation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsulation genes (rep and cap genes), into a cell line which is infected with a human helper virus (for example an adenovirus). The AAV recombinants that are produced are then purified by standard techniques.

The invention also relates, therefore, to an AAV-derived recombinant virus whose genome encompasses a sequence encoding a nucleic acid encoding a polypeptide of the invention flanked by the AAV ITRs. The invention also relates to a plasmid encompassing a sequence encoding a nucleic acid encoding a polypeptide of the invention flanked by two ITRs from an AAV. Such a plasmid can be used as it is for transferring the nucleic acid sequence, with the plasmid, where appropriate, being incorporated into a liposomal vector (pseudo-virus).

Retrovirus Vectors

In another embodiment, the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses that infect dividing cells. The retrovirus genome includes two LTRs, an encapsulation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsulation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). By way of example of a line which can be used for the preparation of defective recombinant retroviruses, there may be mentioned the CRIP line (Danos and Mulligan, PNAS 85 (1988) 6460). Next, the viruses that have multiplied are recovered and purified according to conventional molecular biology techniques. In addition, the recombinant retroviral vectors can contain modifications within the LTRs for suppressing transcriptional activity as well as extensive encapsulation sequences which may include a part of the gag gene (Bender et al., J. Virol. 61 (1987) 1639). Recombinant retroviral vectors are purified by standard techniques known to those having ordinary skill in the art.

Retroviral vectors can be constructed to function as infections particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Targeted gene delivery is described in International Patent Publication WO 95/28494, published October 1995.

Non-Viral Vectors

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., Proc. Natl. Acad. Sci. U.S.A. 84:7413–7417 (1987); see Mackey, et al., Proc. Natl. Acad. Sci. U.S.A. 85:8027–8031 (1988); Ulmer et al., Science 259:1745–1748 (1993)]. The use of cationic lipids may promote encapsulation of negatively charged nucleic acids, and also promote fusion with negatively charged cell membranes [Felgner and Ringold, Science 337:387–388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid (see U.S. Pat. Nos. 5,693,622, 5,589, 466 and 5,580,859). Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963–967 (1992); Wu and Wu, J. Biol. Chem. 263: 14621–14624 (1988); Hartmut et al., Canadian Patent Application No. 2,012,311, filed Mar. 15, 1990; Williams et al., Proc. Natl. Acad. Sci. USA 88:2726–2730 (1991)]. Receptor-mediated DNA delivery approaches can also be used [Curiel et al., Hum. Gene Ther. 3:147–154 (1992); Wu and Wu, J. Biol. Chem. 262:4429–4432 (1987)]. Preferred naked DNA vectors include pCOR plasmids having a conditional origin of replication (see WO97/10343), and minicircle plasmids lacking an origin of replication and a marker gene (see WO96/26270).

Recombinant Host Cells of the Invention

The present invention also relates to the use of cells genetically modified ex vivo with a virus according to the invention, or of cells producing such viruses, implanted in the body, allowing a prolonged and effective expression in vivo of a biologically active polypeptide according to the invention.

The present invention shows that it is possible to incorporate a nucleic acid encoding a polypeptide according to the invention into a viral vector, and that these vectors make it possible to effectively express a biologically active, mature polypeptide. More particularly, the invention shows that the in vivo expression of a polypeptide according to the invention may be obtained by direct administration of an adenovirus or by implantation of a producing cell or of a cell genetically modified by an adenovirus or by a retrovirus incorporating such a nucleic acid.

In this regard, another subject of the invention relates to any isolated mammalian cell infected with one or more defective recombinant viruses according to the invention. More particularly, the invention relates to any population of human cells infected with these viruses. These may be in particular cells of blood origin (totipotent stem cells or precursors), fibroblasts, myoblasts, hepatocytes, keratinocytes, smooth muscle and endothelial cells, glial cells and the like.

Another subject of the invention relates to an implant comprising isolated mammalian cells infected with one or more defective recombinant viruses according to the invention or cells producing recombinant viruses, and an extracellular matrix. Preferably, the implants according to the invention comprise $10^5$ to $10^{10}$ cells. More preferably, they comprise $10^6$ to $10^8$ cells.

More particularly, in the implants of the invention, the extracellular matrix comprises a gelling compound and optionally, a support allowing the anchorage of the cells.

The invention also relates to an isolated recombinant host cell comprising a nucleic acid of the invention, and more particularly, a nucleic acid comprising either one of SEQ ID NOs: 1 or 9, or of a complementary polynucleotide sequence.

The invention also relates to an isolated recombinant host cell comprising a nucleic acid of the invention, and more particularly a nucleic acid comprising a nucleotide sequence as depicted in either SEQ ID NOs: 1 or 9, or of a complementary polynucleotide sequence.

The invention also relates to an isolated recombinant host cell comprising a nucleic acid encoding a polypeptide comprising an amino acid sequence of either one of SEQ ID NOs: 8 or 10.

According to another aspect, the invention also relates to an isolated recombinant host cell comprising a recombinant vector according to the invention. Therefore, the invention also relates to a recombinant host cell comprising a recombinant vector comprising any of the nucleic acids of the invention.

Specifically, the invention relates to an isolated recombinant host cell comprising a recombinant vector comprising a nucleic acid comprising either one of SEQ ID NOs: 1 or 9, or of a complementary polynucleotide sequence.

The invention also relates to an isolated recombinant host cell comprising a recombinant vector comprising a nucleic acid comprising a polynucleotide sequence as depicted in either one of SEQ ID NOs: 1 or 9, or of a complementary polynucleotide sequence.

The invention also relates to an isolated recombinant host cell comprising a recombinant vector comprising a nucleic acid encoding a polypeptide comprising an amino acid sequence of either one of SEQ ID NOs: 8 or 10.

The preferred host cells according to the invention are for example the following:
  a) prokaryotic host cells: strains of *Escherichia coli* (strain DH5-α), of *Bacillus subtilis*, of *Salmonella typhimurium*, or strains of genera such as *Pseudomonas, Streptomyces* and *Staphylococcus*;
  b) eukaryotic host cells: HeLa cells (ATCC No. CCL2), Cv 1 cells (ATCC No. CCL70), COS cells (ATCC No. CRL 1650), Sf-9 cells (ATCC No. CRL 1711), CHO cells (ATCC No. CCL-61) or 3T3 cells (ATCC No. CRL-6361).

Pharmaceutical Compositions and Delivery

The present invention also relates to pharmaceutical compositions. Such compositions may comprise a polypeptide, nucleic acid, recombinant vector, recombinant virus, recombinant host cell, or implant of the invention, as defined above, and a pharmaceutically acceptable excipient, carrier or vehicle. The compositions of the invention are particularly suitable for formulation of biological material for gene therapy. Thus, in a preferred embodiment, the composition comprises a nucleic acid encoding a human ngn3 protein or polypeptide comprising amino acid sequence SEQ ID NO: 10.

Any vector, viral or non-viral, of the invention will preferably be introduced in vivo in a pharmaceutically acceptable excipient, vehicle or carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The pharmaceutical compositions of the invention may be formulated for the purpose of topical, oral, parenteral, intranasal, intravenous, intramuscular, subcutaneous, intraocular, and the like, administration.

Preferably, the pharmaceutical compositions contain pharmaceutically acceptable vehicles for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on addition, as appropriate, of sterilized water or of physiological saline, enable injectable solutions to be formed.

The compositions may be in particular isotonic, sterile, saline solutions (monosodium or disodium phosphate, sodium, potassium, calcium or magnesium chloride and the like or mixtures of such salts), or dry, especially freeze-dried compositions that upon addition, depending on the case, of sterilized water or physiological saline, allow the constitution of injectable solutions.

The preferred sterile injectable preparations can be a solution or suspension in a nontoxic parenterally acceptable solvent or diluent. Examples of pharmaceutically acceptable carriers or vehicles are saline, buffered saline, isotonic saline (e.g., monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The doses of nucleic acids of the invention, either alone or incorporated in a vector, used for administration can be adjusted in accordance with different parameters, and in particular in accordance with the mode of administration used, the pathology in question, the gene to be expressed or the desired treatment period. Generally speaking, in the case of the recombinant viruses according to the invention, these are formulated and administered in the form of doses of between $10^4$ and $10^{14}$ pfu, and preferably $10^6$ to $10^{10}$ pfu. The term pfu (plaque forming unit) corresponds to the infectious power of a solution of virus, and is determined by infection of a suitable cell culture and measurement, generally after 48 hours, of the number of infected cell plaques. The techniques of determination of the pfu titre of a viral solution are well documented in the literature.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The composition of the invention may be introduced parenterally or transmucosally, e.g., orally, nasally, vaginally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. The administration of the composition may be introduced by injection directly into the site to be treated, in particular, into the nervous system.

The preferred route of administration to the nervous system is by direct injection. The nervous system can be imaged using any of the techniques available in the art, such as magnetic resonance imaging or computer-assisted tomography, and the therapeutic composition administered by stereotactic injection, for example.

In yet another embodiment, a composition comprising a human ngn3 polypeptide, or nucleic acid encoding the polypeptide, can be delivered in a controlled release system. For example, the nucleic acid or polypeptide may be administered using intravenous infusion, an implantable osmotic pump, a transdermal patch, liposomes, or other modes of administration. In one embodiment, a pump may be used [see Langer, supra; Sefton, *CRC Crit. Ref.*

Biomed. Eng. 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the heart, thus requiring only a fraction of the systemic dose [see, e.g., Goodson, in *Medical Applications of Controlled Release*, supra, vol. 2, pp. 115–138 (1984)]. Other controlled release systems are discussed in the review by Langer [*Science* 249:1527–1533 (1990)].

Thus, the compositions of the invention can be delivered by intravenous, intraarterial, intraperitoneal, intramuscular, or subcutaneous routes of administration. Alternatively, the compositions, properly formulated, can be administered by nasal or oral administration. A constant supply of the biological material can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

An organism in whom administration of a biological material within the scope of the invention is administered is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The invention relates to the use of a polypeptide, nucleic acid, recombinant vector, recombinant virus, recombinant host cell, or implant according to the invention for the manufacture or preparation of a medicament or pharmaceutical composition intended for the prevention or treatment of a patient or subject suffering from a pathology, dysfunction, disorder, or condition affecting the nervous system.

The invention relates to the use of a polypeptide according to the invention, preferably a polypeptide having an amino acid sequence of either one of SEQ ID NOs: 8 or 10 for the manufacture or preparation of a medicament or pharmaceutical composition intended for the prevention or treatment of a patient or subject suffering from a pathology, dysfunction, disorder, or condition affecting the nervous system.

The invention also relates to the use of a nucleic acid according to the invention, preferably a nucleic acid encoding a polypeptide having an amino acid sequence of either one of SEQ ID NOs: 8 or 10 for the manufacture or preparation of a medicament or pharmaceutical composition intended for the prevention or treatment of a patient or subject suffering from a pathology, dysfunction, disorder, or condition affecting the nervous system.

The invention also relates to the use of a recombinant vector according to the invention, preferably a recombinant vector comprising a nucleic acid encoding a polypeptide having an amino acid sequence of either one of SEQ ID NOs: 8 or 10, for the manufacture or preparation of a medicament or pharmaceutical composition intended for the prevention or treatment of a patient or subject suffering from a pathology, dysfunction, disorder, or condition affecting the nervous system.

The invention also relates to the use of a defective recombinant virus according to the invention, preferably a defective recombinant virus comprising a nucleic acid encoding a polypeptide having an amino acid sequence of either one of SEQ ID NOs: 8 or 10, for the manufacture or preparation of a medicament or pharmaceutical composition intended for the prevention or treatment of a patient or subject suffering from a pathology, dysfunction, disorder, or condition affecting the nervous system. Thus, the present invention also relates to a pharmaceutical composition comprising one or more defective recombinant viruses according to the invention.

The invention also relates to the use of a recombinant host cell according to the invention, preferably a recombinant host cell comprising a nucleic acid encoding a polypeptide having an amino acid sequence of either one of SEQ ID NOs: 8 or 10, for the manufacture or preparation of a medicament or pharmaceutical composition intended for the prevention or treatment of a patient or subject suffering from a pathology, dysfunction, disorder, or condition affecting the nervous system.

The invention also relates to the use of an implant according to the invention, preferably an implant comprising a recombinant host cell comprising a nucleic acid encoding a polypeptide having an amino acid sequence of either one of SEQ ID NOs: 8 or 10, for the manufacture or preparation of a medicament or pharmaceutical composition intended for the prevention or treatment of a patient or subject suffering from a pathology, dysfunction, disorder, or condition affecting the nervous system.

The present invention also relates to the use of cells genetically modified ex vivo with a virus according to the invention, or of producing cells such as viruses, implanted in the body, allowing a prolonged and effective expression in vivo of a biologically active polypeptide according to the invention, preferably a polypeptide having an amino acid sequence of either one of SEQ ID NOs: 8 or 10.

The invention also relates to the use of a polypeptide according to the invention, preferably a polypeptide having an amino acid sequence of either one of SEQ ID NOs: 8 or 10, to control, influence, and/or participate in the expression of a gene.

The invention also relates to the use of a nucleic acid according to the invention, preferably a nucleic acid comprising a polynucleotide sequence of either one of SEQ ID NOs: 1 or 9, for the manufacture or preparation of a medicament or pharmaceutical composition intended for the prevention or treatment of a patient or subject suffering from a pathology, dysfunction, disorder, or condition affecting the nervous system.

The invention also relates to the use of a recombinant vector according to the invention, preferably comprising a nucleic acid comprising a polynucleotide sequence of either one of SEQ ID NOs: 1 or 9, for the manufacture or preparation of a medicament or pharmaceutical composition intended for the prevention or treatment of a patient or subject suffering from a pathology, dysfunction, disorder, or condition affecting the nervous system.

Nucleotide Probes and Primers of the Invention

Nucleotide probes and primers hybridizing with a nucleic acid (genomic DNA, messenger RNA, cDNA) according to the invention also form part of the invention.

The definition of a nucleotide probe or primer according to the invention therefore covers oligonucleotides that hybridize, under the high stringency hybridization conditions defined above, with a polynucleotide sequence of a nucleic acid according to the invention, or a complementary polynucleotide sequence.

According to the invention, nucleic acid fragments derived from a polynucleotide according to the invention are useful for the detection of the presence of at least one copy of a bHLH nucleic acid according to the invention, or of a fragment or of a variant (containing a mutation or a polymorphism) thereof in a sample.

According to the invention, nucleic acid fragments derived from a nucleic acid comprising a polynucleotide sequence of either one of SEQ ID NOs: 1 or 9, or of a complementary polynucleotide sequence, are useful for the detection of the presence of at least one copy of a nucleotide sequence of a bHLH nucleic acid according to the invention, or of a fragment or of a variant (containing a mutation or a polymorphism) thereof in a sample. Nucleotide probes and primers hybridizing with a nucleic acid sequence of a nucleic acid (genomic DNA, messenger RNA, cDNA) that encodes a polypeptide comprising an amino acid sequence comprising SEQ ID NO: 8 or SEQ ID NO: 10, also form part of the invention.

The nucleotide probes or primers according to the invention comprise at least 8 consecutive nucleotides of a nucleic acid comprising a polynucleotide sequence of a) SEQ ID NO: 1, or of a complementary polynucleotide sequence, or b) SEQ ID NO: 9, or of a complementary polynucleotide sequence.

Preferably, nucleotide probes or primers according to the invention will have a length of at least 10, 12, 15, 18, 20 to 25, 35, 40, 50, 70, 80, 100, 200, 500, 1000, or 1500 consecutive nucleotides of a nucleic acid according to the invention, in particular of a nucleic acid comprising a polynucleotide sequence of a) SEQ ID NO: 1, or of a complementary polynucleotide sequence, or b) SEQ ID NO: 9, or of a complementary polynucleotide sequence.

Alternatively, a nucleotide probe or primer according to the invention will consist of and/or comprise a fragment having a length of 8, 10, 12, 15, 18, 20, 25, 35, 40, 50, 100, 200, 500, 1000, or 1500 consecutive nucleotides of a nucleic acid according to the invention, more particularly of a nucleic acid comprising a polynucleotide sequence of a) SEQ ID NO: 1, or of a complementary polynucleotide sequence, or b) SEQ ID NO: 9, or of a complementary polynucleotide sequence.

The preferred probes and primers according to the invention comprise all or part of a polynucleotide sequence comprising any one of SEQ ID NOs: 1, 2, 3, 4, 5, 9, 11, 12, 14, 15, 16, 17, 18, 19, 21, 23, 24, or 25, or of a complementary polynucleotide sequence.

The nucleotide primers according to the invention may be used to amplify any one of the nucleic acids according to the invention, and more particularly a nucleic acid comprising a polynucleotide sequence of either one of SEQ ID NOs: 1 or 9, or of a complementary polynucleotide sequence.

Alternatively, the nucleotide primers according to the invention may be used to amplify a nucleic acid fragment or variant of a nucleic acid comprising a polynucleotide sequence of either one of SEQ ID NOs: 1 or 9, or of a complementary polynucleotide sequence.

A nucleotide primer or probe according to the invention may be prepared by any suitable method well known to persons skilled in the art, including by cloning and action of restriction enzymes or by direct chemical synthesis according to techniques such as the phosphodiester method by Narang et al. (Methods Enzymol, 68:90–98, 1979) or by Brown et al. (Methods Enzymol, 68:109–151, 1979), the diethylphosphoramidite method by Beaucage et al. (Tetrahedron Lett, 22: 1859–1862, 1981) or the technique on a solid support described in EU patent No. EP0,707,592.

Each of the nucleic acids according to the invention, including the oligonucleotide probes and primers described above, may be labeled, if desired, by incorporating a marker which can be detected by spectroscopic, photochemical, biochemical, immunochemical or chemical means. For example, such markers may consist of radioactive isotopes ($^{32}$P, $^{33}$P, $^{3}$H, $^{35}$S), fluorescent molecules (5-bromodeoxyunridine, fluorescein, acetylaminofluorene, digoxigenin) or ligands such as biotin. The labeling of the probes is preferably carried out by incorporating labeled molecules into the polynucleotides by primer extension, or alternatively by addition to the 5' or 3'ends. Examples of nonradioactive labeling of nucleic acid fragments are described in particular in French patent No. 78 109 75 or in the articles by Urdea et al. (Nucleic Acids Research, 11:4937–4957, 1988) or Sanchez-Pescador et al. (J. Clin. Microbiol., 26(10):1934–1938, 1988).

Preferably, the nucleotide probes and primers according to the invention may have structural characteristics of the type to allow amplification of the signal, such as the probes described by Urdea et al. (Nucleic Acids Symp Ser., 24:197–200, 1991) or alternatively in European patent No. EP0 225,807 (CHIRON).

The oligonucleotide probes according to the invention may be used in particular in Southern-type hybridizations with the genomic DNA or alternatively in hybridizations with the corresponding messenger RNA when the expression of the corresponding transcript is sought in a sample.

The probes and primers according to the invention may also be used for the detection of products of PCR amplification or alternatively for the detection of mismatches.

Nucleotide probes or primers according to the invention may be immobilized on a solid support. Such solid supports are well known to persons skilled in the art and comprise surfaces of wells of microtiter plates, polystyrene beds, magnetic beds, nitrocellulose bands or microparticles such as latex particles.

Methods for Amplifying and Detecting Nucleic Acids Encoding Polypeptides of the Invention The invention also relates to means for the amplification and detection of nucleic acids according to the invention, preferably a nucleic acid encoding a polypeptide comprising an amino acid sequence of either one of SEQ ID NO: 8 or SEQ ID NO: 10.

A preferred embodiment of the present invention relates to a method of amplifying a nucleic acid according to the invention, and more particularly a nucleic acid comprising a polynucleotide sequence of SEQ ID NOs: 1 or 9, or of a complementary polynucleotide sequence; or a nucleic acid fragment or variant thereof contained in a sample, wherein said method comprises the steps of:
  a) bringing the sample in which the presence of the target nucleic acid is suspected into contact with a pair of nucleotide primers whose hybridization position is located respectively on the 5'side and on the 3'side of the region of the target nucleic acid whose amplification is sought, in the presence of the reagents necessary for the amplification reaction; and
  b) detecting the amplified nucleic acids.

The present invention also relates to a method of detecting the presence of a nucleic acid in a sample, wherein the nucleic acid comprises a polynucleotide sequence of SEQ ID NOs: 1 or 9, or of a complementary polynucleotide sequence; or a nucleic acid fragment or variant thereof, said method comprising the steps of:

1) bringing one or more nucleotide probes according to the invention into contact with the sample to be tested;
  2) detecting the complex which may have formed between the probe(s) and the nucleic acid present in the sample.

According to a specific embodiment of the method of detection according to the invention, the oligonucleotide probes and primers are immobilized on a support.

According to another aspect, the oligonucleotide probes and primers comprise a detectable marker.

The invention relates, in addition, to a box or kit for detecting the presence of a nucleic acid according to the invention in a sample, said box or kit comprising:
  a) one or more nucleotide probe(s) or primer(s) as described above;
  b) where appropriate, the reagents necessary for the hybridization reaction.

According to a first aspect, the detection box or kit is characterized in that the probe(s) or primer(s) are immobilized on a support.

According to a second aspect, the detection box or kit is characterized in that the oligonucleotide probes comprise a detectable marker.

According to a specific embodiment of the detection kit described above, such a kit will comprise a plurality of oligonucleotide probes and/or primers in accordance with the invention which may be used to detect a target nucleic acid of interest or alternatively to detect mutations in the coding regions or the non-coding regions of the nucleic acids according to the invention.

Another subject of the invention is a box or kit for amplifying all or part of a nucleic acid comprising a polynucleotide sequence of SEQ ID NOs: 1 or 9, or of a complementary polynucleotide sequence, wherein said box or kit comprises:
  1) a pair of nucleotide primers in accordance with the invention, whose hybridization position is located respectively on the 5' side and 3' side of the target nucleic acid whose amplification is sought; and optionally,
  2) reagents necessary for an amplification reaction.

Such an amplification box or kit will preferably comprise at least one pair of nucleotide primers as described above.

The invention also relates to a box or kit for detecting the presence of a nucleic acid according to the invention in a sample, said box or kit comprising:
  a) one or more nucleotide probes according to the invention;
  b) where appropriate, reagents necessary for a hybridization reaction.

According to a first aspect, the detection box or kit is characterized in that the nucleotide probe(s) and primer(s) are immobilized on a support.

According to a second aspect, the detection box or kit is characterized in that the nucleotide probe(s) and primer(s) comprise a detectable marker.

According to a specific embodiment of the detection kit described above, such a kit will comprise a plurality of oligonucleotide probes and/or primers in accordance with the invention that may be used to detect target nucleic acids of interest.

According to preferred embodiment of the invention, the target nucleic acid comprises a polynucleotide sequence of SEQ ID NOs: 1 or 9, or of a complementary polynucleotide sequence.

Alternatively, the target nucleic acid is a nucleic acid fragment or variant of a nucleic acid comprising a polynucleotide sequence of SEQ ID NOs: 1 or 9, or of a complementary polynucleotide sequence.

According to a preferred embodiment, two primers according to the invention comprise all or part of SEQ ID NOs: 4 and 13, making it possible to amplify the region of nucleotides 750–1460 of SEQ ID NO: 1, or a nucleic acid having a complementary polynucleotide sequence.

According to a preferred embodiment, two primers according to the invention comprise all or part of SEQ ID NOs: 5 and 13, making it possible to amplify the region of nucleotides 777–1460 of SEQ ID NO: 1, or a nucleic acid having a complementary polynucleotide sequence.

According to a preferred embodiment, two primers according to the invention comprise all or part of SEQ ID NOs: 5 and 13, making it possible to amplify the region of nucleotides 640–1330 of SEQ ID NO: 9, or a nucleic acid having a complementary polynucleotide sequence.

According to a preferred embodiment, two primers according to the invention comprise all or part of SEQ ID NOs: 5 and 25, making it possible to amplify the region of nucleotides 640–1330 of SEQ ID NO: 9, or a nucleic acid having a complementary polynucleotide sequence.

According to a preferred embodiment, two primers according to the invention comprise all or part of SEQ ID NOs: 24 and 25, making it possible to amplify the region of nucleotides 1–1330 of SEQ ID NO: 9, or a nucleic acid having a complementary polynucleotide sequence.

According to another preferred embodiment, a primer according to the invention comprises, generally, all or part of any one of SEQ ID NOs: 1, 2, 3, 4, 5, 9, 11, 12, 14, 15, 16, 17, 18, 19, 21, 23, 24, or 25, or a complementary sequence.

Thus, the probes according to the invention, immobilized on a support, may be ordered into matrices such as "DNA chips". Such ordered matrices have in particular been described in U.S. Pat. No. 5,143,854, in published PCT applications WO 90/15070 and WO 92/10092.

Support matrices on which oligonucleotide probes have been immobilized at a high density are for example described in U.S. Pat. No. 5,412,087 and in published PCT application WO 95/11995.

The nucleotide primers according to the invention may be used to amplify any one of the nucleic acids according to the invention, or a complementary polynucleotide sequence. Alternatively, the nucleotide primers according to the invention may be used to amplify a nucleic acid fragment or variant of a nucleic acid according to the invention, or a complementary polynucleotide sequence.

Another subject of the invention relates to a method of amplifying a nucleic acid according to the invention, or a complementary polynucleotide sequence, contained in a sample, said method comprising the steps of:

a) bringing the sample in which the presence of the target nucleic acid is suspected into contact with a pair of nucleotide primers whose hybridization position is located respectively on the 5' side and on the 3' side of the region of the target nucleic acid whose amplification is sought, in the presence of the reagents necessary for the amplification reaction; and b) detecting the amplified nucleic acids.

To carry out the amplification method as defined above, use will be preferably made of any of the nucleotide primers described above.

The subject of the invention is, in addition, a box or kit for amplifying all or part of a nucleic acid according to the invention, or a complementary polynucleotide sequence, said box or kit comprising:

a) a pair of nucleotide primers in accordance with the invention, whose hybridization position is located respectively on the 5' side and 3' side of the target nucleic acid whose amplification is sought; and optionally, b) reagents necessary for the amplification reaction.

Such an amplification box or kit will preferably comprise at least one pair of nucleotide primers as described above.

The invention also relates to a box or kit for detecting the presence of a nucleic acid according to the invention in a sample, said box or kit comprising:

a) one or more nucleotide probes according to the invention;

b) where appropriate, reagents necessary for a hybridization reaction.

According to a first aspect, the detection box or kit is characterized in that the nucleotide probe(s) and primer(s) are immobilized on a support.

According to a second aspect, the detection box or kit is characterized in that the nucleotide probe(s) and primer(s) comprise a detectable marker.

According to a specific embodiment of the detection kit described above, such a kit will comprise a plurality of oligonucleotide probes and/or primers in accordance with the invention which may be used to detect target nucleic acids of interest or alternatively to detect mutations in the coding regions or the non-coding regions of the nucleic acids according to the invention.

According to preferred embodiment of the invention, the target nucleic acid comprises a polynucleotide sequence of SEQ ID NOs: 1 or 9, or of a complementary polynucleotide sequence.

Alternatively, the target nucleic acid is a nucleic acid fragment or variant of a nucleic acid comprising a polynucleotide sequence of SEQ ID NOs: 1 or 9, or of a complementary polynucleotide sequence.

According to a preferred embodiment, a primer according to the invention comprises, generally, all or part of any one of SEQ ID NOs: 1, 2, 3, 4, 5, 9, 11, 12, 14, 15, 16, 17, 18, 19, 21, 23, 24, or 25, or a complementary sequence.

Screening Assays

Identification and isolation of a gene encoding a polypeptide of the invention provides for expression of the polypeptide in quantities greater than can be isolated from natural sources, or in indicator cells that are specially engineered to indicate the activity of a polypeptide of the invention expressed after transfection or transformation of the cells. Accordingly, in addition to rational design of agonists and antagonists based on the structure of a polypeptide of the invention, the present invention contemplates an alternative method for identifying specific ligands of the polypeptide using various screening assays known in the art.

Basic helix-loop-helix proteins play a role in cell differentiation and/or cell fate determination by regulating or inducing transcription of key genes. Therefore, agonists and antagonists of a polypeptide of the present invention will be expected to improve or decrease its transcription factor activity.

The invention provides methods for screening small molecules and compounds that act on a basic helix-loop-helix protein to identify agonists and antagonists of Relax or hngn3 polypeptides that can improve, reduce, or inhibit neurogenesis, or a function of the nervous system, or a function of the endocrine system, in particular, the pancreas from a therapeutic point of view. For example, hngn3 may be implicated in the transforming process that leads to some neuroectodermal and/or pancreatic tumors. In these cases, inhibiton of bHLH activity could be of great therapeutic value. Furthermore, activation of hngn3 may be useful to generate in vitro or in vivo specific neuronal cells and endocrine pancreatic cells. It has recently been reported that the overexpression of ngn3 in the developing pancreas yields an increase number of insulin producing cells.[32] Thus, the activation of hngn3 polypeptides may be useful in the treatment of type 1 diabetes mellitus. In general, these methods are useful to identify small molecules and compounds for therapeutic use in the treatment of a disease, condition, disorder, pathology, or dysfunction of the nervous system, or the endocrine system, specifically, the pancreatic organ.

Thus, the present invention relates to a method of screening for antagonists or agonists of the polypeptides according to the invention. Preferably, the method of screening for antagonists or agonists of the polypeptides according to the invention is directed toward identifying an antagonist or agonist of a polypeptide comprising an amino acid sequence of either one of SEQ ID NO: 8 or SEQ ID NO: 10.

Therefore, the invention also relates to the use of a polypeptide according to the invention or a cell expressing a polypeptide according to the invention, for screening active ingredients for the prevention or treatment of a disease, condition, disorder, pathology, or dysfunction of the nervous system. An active site and oligopeptide or immunogenic fragments of a polypeptide according to the invention can serve for screening product libraries by a whole range of existing techniques. The polypeptide fragment used in this type of screening may be free in solution, bound to a solid support, at the cell surface or in the cell. The formation of the binding complexes between the polypeptide fragments and the tested agent can then be measured.

Another product screening technique that may be used in high-flux screenings giving access to products having affinity for the protein of interest is described in application WO84/03564. In this method, applied to a polypeptide according to the invention, various products are synthesized on a solid surface. These products react with the polypeptide or fragment thereof and the complex is washed. The products binding the polypeptide are then detected by methods known to persons skilled in the art. Non-neutralizing antibodies can also be used to capture a peptide and immobilize it on a support.

Another possibility is to perform a product screening method using a neutralizing antibody competition, a polypeptide according to the invention, and a product potentially binding the polypeptide. In this manner, the antibodies may be used to detect the presence of a peptide having a common antigenic unit with the polypeptide or protein according to the invention.

Accordingly, this invention relates to the use of any method of screening products, i.e., compounds, small molecules, and the like, this being in all synthetic or cellular types, that is to say of mammals, insects, bacteria, or yeasts expressing constitutively or having incorporated a rat Relax or human ngn3 encoding nucleic acid.

The present invention also relates to the use of such a system for screening molecules that modulate the activity of a polypeptide according to the invention. Thus, the invention relates to methods of screening and identifying a modulator, agonist, or antagonist of a polypeptide according to the invention in a sample.

Any screening technique known in the art can be used to screen for agonists or antagonists of the polypeptides of the invention. For example, a suitable isolated cell or cell line that expresses a polypeptide according to the invention, preferably human ngn3, can be transfected with a nucleic acid encoding a marker gene, such as β-galactosidase (β-gal). The isolated cell or cell line may express the polypeptide of the invention either naturally or after transfection of a nucleic acid encoding the polypeptide. The cell or cell line is then exposed to a test solution or sample comprising a potential agonist or antagonist, and then stained for β-galactosidase activity. The presence of more β-gal positive cells relative to control cells not exposed to the test solution or sample is an indication of the presence of an agonist in the test solution or sample. Conversely, the presence of less β-gal positive cells relative to control cells not exposed to the test solution or sample is an indication of the presence of an antagonist in the test solution or sample.

The present invention relates to methods of identifying a modulator, agonist, or antagonist of a polypeptide according to the invention in a sample comprising
  a) obtaining a cell, for example a cell line, that, either naturally or after transfecting the cell with a nucleic acid encoding a polypeptide according to the invention, expresses a polypeptide according to the invention,
  b) transfecting the cell with a nucleic acid encoding a marker gene, such as β-galactosidase (β-gal),
  c) incubating the cell of step b) with a test solution or sample comprising a potential modulator, agonist or antagonist, d) measuring the amount of β-galactosidase activity, and
  e) comparing the amount of β-galactosidase activity measured in step d) with an amount of β-galactosidase activity measured with a cell that has not been previously incubated in the presence of the candidate modulator, agonist, or antagonist compound for the polypeptide according to the invention.

Another method of the present invention for identifying an agonist or antagonist of the ngn3 polypeptide is based on Applicant's discovery that ngn3 polypeptide specifically activates its own promoter as shown in the spinal cord and pancreas. Applicants have recognized that the expression of ngn3 is strictly dependent on the ngn3 protein. To date, no other members of the bHLH family have been found to activate or modulate the endogenous ngn3 promoter. According to the novel method in the present invention, the ngn3 responsive element located within the ngn3 promoter may be placed upstream of a reporter gene, for example, β-galactosidase, firefly luciferase, or green fluorescent protein, and be used as a specific marker to assay the level of activity of the ngn3 polypeptide in the presence of an agonist or antagonist in a cell that expresses a known amount of ngn3 protein. The compound that modulates the endogenous activity of the ngn3 polypeptides will modify the expression of the reporter gene. The cell may be a primary culture cell or a cell line that either naturally or after transfecting with a nucleic acid encoding a ngn3 polypeptide according to the invention, expresses the polypeptide according to the invention.

In a specific embodiment, the polypeptide comprises an amino acid sequence of SEQ ID NO: 8 or SEQ ID NO: 10.

According to a first aspect of the above screening methods, the cells used are cells naturally expressing a polypeptide according to the invention. Preferably, the cell expresses a polypeptide comprising an amino acid sequence of SEQ ID NO: 8 or SEQ ID NO: 10. The cells may be primary culture cells obtained from a population of embryonic pancreatic epithelium and/or ventral spinal cord, for example.

According to a second aspect, the cells used in the screening methods described above may be cells not naturally expressing, or alternatively expressing at a low level, a polypeptide according to the invention, said cells being transfected with a recombinant vector according to the invention capable of directing the expression of a nucleic acid encoding the polypeptide. Preferably, the cell expresses a polypeptide comprising an amino acid sequence of SEQ ID NO: 8 or SEQ ID NO: 10.

According to a third aspect of the above screening methods, the polypeptide according to the invention may be a recombinantly produced polypeptide. Preferably, the recombinantly produced polypeptide comprises an amino acid sequence of SEQ ID NO: 8 or SEQ ID NO: 10.

The present invention contemplates screens for small molecule ligands or ligand analogs and mimics, as well as screens for natural ligands that bind to and agonize or antagonize a polypeptide of the invention in vivo. For example, natural products libraries can be screened using assays of the invention for molecules that agonize or antagonize the polypeptide's activity.

Knowledge of the primary sequences of Relax and hngn3, and the similarity of these sequences with proteins of known function, can provide an initial clue as to the inhibitors or antagonists of the polypeptides of the invention. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, Volume 5*, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for ligands of the polypeptides according to the present invention.

The screening can be performed with recombinant cells that express a polypeptide of the invention, or alternatively, using purified protein, e.g., produced recombinantly, as described above. For example, labeled, soluble Relax or hngn3 can be used to screen libraries, as described in the foregoing references.

In one embodiment, a polypeptide of the invention may be directly labeled. In another embodiment, a labeled secondary reagent may be used to detect binding of the polypeptide of the invention to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two-color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two color assays may be performed with two or more colored latex beads, or fluorophores that emit at different wavelengths. Labeled may be detected visually or by mechanical/optical means. Mechanical/optical means include fluorescence activated sorting, i.e., analogous to FACS, and micromanipulator removal means.

As exemplified herein, the level of a polypeptide of the invention can be evaluated by metabolic labeling of the proteins. As the metabolic labeling occurs during in vitro incubation of the tissue biopsy in the presence of culture medium supplemented with [$^{35}$S]-methionine, the level of each of the markers detected may be affected by the in vitro conditions. In addition to metabolic (or biosynthetic) labeling with [$^{35}$S]-methionine, the invention further contemplates labeling with [$^{14}$C]-amino acids and [$^3$H]-amino acids (with the tritium substituted at non-labile positions). Thus, a sample or library of compounds can be directly analyzed after labeling of the proteins therein, e.g., by colorimetric staining using silver, gold, coomassie blue, or amidoschwartz, to mention a few techniques; isotopic labeling, e.g., with [$^{32}$P]-orthophosphate, [$^{125}$I], [$^{131}$I]; fluorescent or chemiluminescent tags; and immunological detection with labeled antibody or specific binding partner of a marker.

The present invention may be better understood by reference to the following non-limiting Examples, which are provided as exemplary of the invention. The examples and figures presented below by way of illustration and with no limitation being implied demonstrate other advantages and characteristics of the present invention.

EXAMPLES

General Molecular Biology Techniques

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extraction with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; ($2^{nd}$ Ed. 1989); Ausubel F. M. et al. (eds), "Current Protocols in Molecular Biology", John Wiley & Sons, New York, 1987].

Conventional cloning vehicles include pBR322 and pUC type plasmids and phages of the M13 series. These may be obtained commercially (Bethesda Research Laboratories).

For ligation, DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of E. coli DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of nucleotide sequences may be performed by the method developed by Sanger et al. [Proc. Natl. Acad. Sci. USA, 74 (1977) 5463–5467] using the kit distributed by Amersham.

Plasmid DNAs may be purified by the Qiagen Plasmid Purification System according to the manufacture's instruction.

Example 1

Direct Amplification by PCR of the Sequences Between the Basic Domains and Helix II with the Aid of Degenerate Oligonucleotides The isolation of the cDNA encoding new transcription factors of the bHLH family is carried out using rat SCG (Rat Superior Cervical Ganglia). Given that the proteins of this family have highly conserved amino acid units, in particular a basic domain followed by Helix I and Helix 2, degenerate oligonucleotides encoding these various conserved regions are chosen. They were therefore selected so as to conserve the basic regions and the Helix II domain of the complex Drosophilia achaete-scute and the bHLH mammalian genes such as Mash-1, Mash-2 and M-Twist. Such oligonucleotides have been used respectively as sense and anti-sense primers on the one hand, to carry out direct screening of an SCG library constructed by PCR, and on the other hand in order to carry out PCRs on SCG ss-cDNAs.

The sense oligonucleotide was chosen from the basic domain of these bHLH proteins; it is more precisely the oligonucleotide corresponding to the following polypeptide fragment: 5'-AATKHGMGIGAGCGCIDKCGCRYG-3' (SEQ ID NO: 2).

The anti-sense oligonucleotide, for its part, was determined from the Helix II domain of the same bHLH proteins. It is the oligonucleotide corresponding to the following polypeptide fragment: 5'-GGCSRDTYTCAGGGTSYBGAYCTT-3' (SEQ ID NO: 3).

The single-stranded cDNA (ss-cDNA) is prepared from 500 ng of denatured polyA RNA derived from the SCG of two-day-old rats.

The PCR amplification is carried out on a mixture comprising, in addition to the PCR buffer (10 mM Tris, pH 8.3, 50 mM Kcl, 2.5 mM MgCl2), 200 µM dNTP, 12.5 µM of each oligonucleotide and about 20 ng of single-stranded (ss)-cDNA. The PCR is carried out by performing successively 3 minutes of denaturation at 94° C.; 2 cycles [94° C. for 30 seconds(sec); 50° C. for 45 sec; 72° C. for 1.5 minutes(min)] followed by 38 cycles (94° C. for 30 sec; 62° C. for 45 sec; 72° C. for 1.5 min). The PCR products are cloned at the SmaI site of pUC19 and the 1500 clones thus obtained analyzed by sequencing. Applicants searched for the presence of a Helix I unit in the amino acid sequence deduced from the nucleotide sequence of these various cDNAs. A large proportion of these cDNAs (670) contain such a unit, and among them, only one corresponds to a new possible member of the bHLH family. The other cDNAs isolated correspond to known bHLH proteins.

The new isolated cDNA, called CIG235 and represented in FIG. 1, corresponds to a fragment of 76 nucleotides (excluding the sequences corresponding to the oligonucleotides introduced by PCR). The alignments of amino acid sequences were performed by authorizing neither insertions nor deletions. These alignments show that this fragment encodes a unit homologous to the Helix I unit of the bHLH proteins. The isolation of the complete cDNA was then undertaken.

Example 2

Isolation of the Complete cDNA Corresponding to CIG235

The isolation of the complete cDNA corresponding to CIG235 was extremely difficult because the mRNA corresponding to CIG235 is very little expressed in the SCG. It even appears that its expression level is close to that of the illegitimate transcription. The technique selected consists, on the one hand, in isolating the 3' end of the cDNA corresponding to CIG235 by anchored PCR and, on the other hand, in isolating the 5' end of this cDNA from the spinal cord of rat embryos at the E12.5 stage.

1. Extension of the cDNA CIG235 in 3' by Anchored PCR.

For that, SCG ss-cDNA were prepared with the RA3' NV primer (random reverse transcription primer carrying the 3' NV anchor) according to the Dumas Milne Edwards et al. method (1995, A Practical Approach Ed McPherson et al., pp 89–118, IRL Press Oxford U.K.). Two specific nested primers are chosen in the bHLH positive clone of 76 nucleotides: CIG5'-1: 5'-AACCTTAACTCCGCGCTGGATGCGC-3' (SEQ ID NO: 4) and CIG5'-2: 5'-CGCGGTGTCCTGC-CCACC-3' (SEQ ID NO: 5).

Applicants then amplified the 3' end of CIG235 by two nested PCRs with the pairs of oligonucleotides CIG5'1 and A3'-1 and then CIG5'2 and A3'-2. The PCR mixture identified in Example 1 is used with only 0.8 µM of each of the oligonucleotides and a denaturation step at 94° C. for 30 sec followed by an extension step at 72° C. for 1.5 min. The "annealing" is carried out for 45 sec with variations in temperature. During the first ten cycles, this temperature is reduced by 1° C. every two cycles from 70° C. to 65° C. and then maintained at 65° C. during 30 cycles. The resulting products are cloned into pUC19 and sequenced. Applicants thus obtained a cDNA of 717 nucleotides, called CIG3', whose 5' part corresponds to the 3' end of the clone CIG235. Analysis of the open reading frames shows that the entire sequence encoding the carboxy-terminal end of the protein was isolated with 321 nucleotides of noncoding 3' region.

2. Isolation of the 5' End Corresponding to CIG3' from the Spinal Cord of Rat Embryos at the E12.5 Stage.

Applicants sought out by in situ hybridization the pattern of expression of the mRNA corresponding to CIG3'. Its expression is estimated at various stages of the embryonic development. The method chosen is that of in situ hybridization on thick rat embryo sections with a digoxygenin-labelled probe. This method is in fact an adaptation of that described for in toto hybridization (1994, A Practical Approach, Ed Wilkinson et al., pp 75–83, IRL Press Oxford U.K.), and makes it possible to rapidly screen whole embryos at numerous different stages.

A high expression of this mRNA was detected in the spinal cord, at embryonic day 12.5 (E12.5). Applicants therefore prepared mRNAs from spinal cord at this stage of development, and carried out the isolation of the 5' end by the SLIC method. A PCR product of 893 nucleotides is isolated and called CIG5'.

The CIG3' and CIG5' cDNAs overlap over a region of 120 nucleotides and form a total cDNA whose size is 1491 nucleotides.

However, given that CIG3' and CIG5' were not isolated from the same tissue, it was necessary to show that the contig generated by the alignment of these two clones corresponded to an existing mRNA and not to a chimera generated by PCR. Applicants therefore verified by PCR, after reverse transcription, that the total mRNA is present in the spinal cord at E12.5. In this tissue, a single PCR amplification makes it possible to visualize this mRNA in its entirety. Furthermore, analysis of the mRNAs by Northern blotting shows that all three of the probes CIG3', CIG5' and total cDNA make it possible to detect a single mRNA of 3.1 kb. Finally, in situ hybridization, the spatiotemporal expression pattern obtained with CIG3' or with the total cDNA is absolutely identical. These three results allow us to assert that CIG3' and CIG5' indeed correspond to two fragments of a same mRNA.

In order to dispense with the point mutations introduced by Taq polymerase, Applicants carried out, on ss-cDNAs of the spinal cord at E12.5, four independent amplifications of the entire cDNA. Applicants were thus able to accurately determine the sequence of this cDNA that is represented in SEQ ID NO: 1.

Analysis of the cDNA sequence shows that Applicants isolated the entire coding region, the noncoding 5' region as well as part of the untranslated 3' region. Furthermore, the expression of the corresponding mRNA is detected in the embryo in the form of longitudinal bands. This characteristic led to this cDNA being designated Relax, for Rat embryonic longitudinal axis.

Example 3

Comparison of Amino Acid Sequences of the bHLH Domain of Relax with Other Proteins of the BHLH Family Analysis of the amino acid sequence deduced from the Relax cDNA clearly indicates that this protein is part of the bHLH family. The bHLH domain of Relax shares 68% identity with the bHLH unit of the protein NeuroD (Lee et al., 1995). Furthermore, it appears that Relax shares more sequence identities with proteins homologous to (Math-1, Akazawa et al., 1995) than with those homologous to AS-C (Mash-1, Johnson et al., 1990) (FIG. 2). However, the total absence of sequence identity, outside the bHLH domain, with the other members of the family reveals that Relax is not the paralogue of an already identified protein. For this reason, Relax probably corresponds to the first member of a new subfamily of bHLH proteins.

Example 4

Characterization of the Transcriptional Activity of the Relax Protein

The amino acid sequence analyses indicate that Relax shares a common structure with proteins of the bHLH family. These proteins are transcription factors. It is therefore important to demonstrate that the Relax cDNA encodes a protein whose characteristics are those of a transcription factor, that is to say that Relax is capable of binding to DNA on the target sites of bHLH factors, and that it can regulate transcription.

1. Proteins of the bHLH Family Form homo- or Heterodimers and Bind Specifically to DNA (Murre et al., 1989, *Cell*, 558, 537–44).

The in vitro characterization of the DNA binding sites has allowed the identification of a consensus hexanucleotide sequence, CANNTG, called E box (Murre et al., 1989). Applicants have shown, by gel migration retardation experiments, that the purified recombinant Relax protein is capable of binding specifically to a sequence containing an E box. To do this, the DNA encoding the Relax protein is inserted between the NdeI and KpnI sites into a vector pFLAG-CTC. After expression of the protein in *Escherichia coli*, the fusion protein Relax-Flag is purified on an affinity column and then used in a binding reaction in the presence of an oligonucleotide containing an E box.

2. The Transcriptional Activity of the Relax Protein, for its Part, was Tested by Cotransfection Experiments in the Cell Line PC12, Derived from Rat Pheochromocytomas.

For that, Applicants used a luciferase reporter gene placed under the control, on the one hand, of a promoter containing an E box (5 kb of the TH promoter) and, on the other hand, of the same promoter containing a mutated E box.

In parallel, Applicants prepared a vector for expressing the Relax protein as follows:
(a) The cDNA encoding the Relax protein (from position 389 to 1235) is inserted between the EcoRI and XhoI sites into the expression vector pcDNA3 downstream of the CMV promoter. The rat TH promoter carrying an E box CAGGTG (SEQ ID NO: 6) at position 197 on a 5 kbp fragment is inserted into the blunt ended HindIII site in the plasmid pKSLuc which becomes 5 kbTH-Luc. The site is mutated into TCCGTG (SEQ ID NO: 7) and the resulting plasmid designated 5 kbTH(Delta E)-Luc.
(b) The plasmid pcDNA3-Relax is cotransfected in various quantities ranging from 0 to 5 pmol, and brought to 5 pmol with empty vector pcDNA3, in PC12 cells ($10^6$ cells/plate) mixed with 1 pmol of plasmid 5 kbTH-Luc, 5 kb-TH(deltaE)-Luc or pKSLuc. To evaluate the transfection efficiency, 0.2 pmol of a vector for expressing the gene encoding the CAT (chloramphenicol acetyltransferase) protence under the control of the RSV promoter are also cotransfected.

Measurement of the luciferase activity, after cotransfection of these vectors with increasing quantities of a vector for expressing the Relax protein, demonstrates that Relax activates the transcription of the reporter gene depending on the quantity of expression vector used and that this activation strictly requires the presence of an intact E box.

Example 5

Characterization of the Sites for Expression of the Relax mRNA During Embryonic Development Applicants systematically analysed, by in situ hybridization, the distribution of the Relax mRNA in rats during embryonic development. To do this, in situ hybridizations in the rat embryo are carried out according to the Wilkinson method with anti-sense riboprobes either in toto or on sections of 250 μm. The riboprobes are prepared in the presence of Ig of linearized plasmid and in the presence of 3.5 nmol of digoxygenin-11-UTP using the Promega riboprobe kit. This detailed analysis shows that the expression of the Relax mRNA is transitory and spatially restricted.

This mRNA is only present in the embryo, between days 11.5 and 18.5 of development. Its expression is restricted to the central nervous system. Indeed, no expression was detected, either in the peripheral nervous system, or outside of the nervous system. Inside the CNS, the Relax mRNA is expressed only in the spinal cord, the posterior brain and the anterior brain.

More precisely, the Relax mRNA is expressed in longitudinal compartments in the spinal cord and the posterior brain.

Its distribution in the spinal cord is restricted therein to two continuous bands of bilateral symmetry, longitudinally organized and restricted, on the D/V axis, to the basal lamina, one at its ventral end, the other at its dorsal end.

In the anterior brain, the Relax mRNAs are located in two groups of cells situated on either side of the optic recess, in the ventral region of the hypothalamus and in the preoptic area. The predominant group of cells expressing Relax is situated in the basal part. Only the few cells of the preoptic area are situated in the wing region. The situation in the anterior brain is similar to that in the spinal cord and the posterior brain. Indeed, the cells expressing Relax are, in all cases, strictly located in the ventricular zone.

Example 6

Characterization of the Moments of Expression of the Relax mRNA During Embryonic Development All the sites of expression of Relax simultaneously belong to E11.5. They disappear progressively from the spinal cord between E16.5 and E18.5, according to a ventrodorsal gradient that follows the progressive reduction of the ventricular zone. In the posterior brain, the expression of Relax switches off, at the same time as that of the median band in the spinal cord. Finally, in the anterior brain, the expression of Relax disappears after E18.5. It is important to underline that the expression of Relax is confined to the ventricular zone and that the temporal window for expression coincides with that for the production of the neurons in these different structures.

Example 7

Isolation of a New cDNA Encoding the Human Neurogenin 3 (hngn3) Homolog

Applicants have shown that the overexpression of Relax, the rat homolog of ngn3, in *Xenopus* embryo, induces the ectopic production of neurons throughout the ectoderm, thereby demonstrating that ngn3 has a neuronal determination function (Examples 1–6 supra and[14]). Here, Applicants report the isolation of the human neurogenin 3 homolog (hngn3).

PCR primers: All PCR primers were chosen with the Oligo 4.0 software program. The nucleotide position of all the primers listed below is given relative to the genomic hngn3 sequence (SEQ ID NO: 9).

ss-cDNA synthesis: Randomly primed ss-cDNAs were synthesized using total RNA extracted from the spinal cord of a 7-week-old human embryo. Total RNA was prepared with RNAble (Eurobio) based on a guanidine/phenol extraction procedure described by Chomczynski and Saachi[27]. The ss-cDNAs were synthesized from 2 μg of denatured total RNA in the following reaction mix: 0.4 μM random hexamer, 2.5 mM dNTP, 4 mM $MgCl_2$, 10 mM Tris, pH 9, 50 mM KCl, 0.1% Triton X-100, 0.01% gelatin, 10 mM DTT, 8 U RNasin and 2.4 U AMV RTase. The mixture was incubated at 42° C. for 1 hour.

Amplification of the hngn3 bHLH domain: PCR was performed using two specific primers deduced from the nucleotide sequences of Relax and ngn3 corresponding to the basic domain: hngn3B (nucleotides 585–602) 5'-CAACGACCGCGAGCGCAA-3' (SEQ ID NO: 11) and to the helix II domain: hngn3HII (nucleotides 722–699) 5'-GCCCAGATGTAGTTGTGGGCGAAG-3' (SEQ ID NO: 12). The PCR mix consisted of 10 mM Tris pH 9, 50 mM KCl, 0.1% Triton X-100, 0.01% gelatin, 1.5 mM $MgCl_2$, 0.8 μM of both primers, 200 μM dNTP, 2.5 U Taq polymerase and one tenth of the previously synthesized ss-cDNAs. Amplification conditions were: 94° C. for 3 min., 60° C. for 2 min., 72° C. for 30 sec. then 29 cycles of 94° C. for 30 sec., 60° C. for 45 sec., 72° C. for 30 sec. The PCR products were subcloned using the pmosBlue PCR cloning system (Amersham) and sequenced.

3' anchored PCR: Randomly primed ss-cDNAs were synthesized as above with a different random primer (RA3'-NV; 5'-TCGTTGAGACTCGTACCAGCAGA GTCAC-GAGAGAGACTACACGGTACTGGNNNNN-3'; SEQ ID NO: 13) to make it possible to carry out the 3' extension experiment described by Ravassard et al.[28]. Two specific nested primers were designed based upon the sequence of the 138 bp fragment corresponding to the bHLH domain of hngn3, hngn35'-1 (nucleotides 663–683): 5'-AGACGACGCGAAGCTCACCA-3' (SEQ ID NO: 14) and hngn35'-2 (nucleotides 675–693): 5'-GCTCACCAAGATCGAGACGCTGCG-3' (SEQ ID NO: 15). Applicants obtained the 3'-extended cDNA by performing two rounds of nested PCR, one with A3'-1: 5'-ATCGTTGAGACTCGTACCAGCAGAG-3' (SEQ ID NO: 16) and hngn35'-1, and the other with A3'-2: 5'-TCG-TACCAGCAGAGTCACGAGAGAG-3' (SEQ ID NO: 17) and hngn35'-2. Applicants used the reaction mix described above. Amplification conditions were: 94° C. for 3 min., 58° C. for 45 sec., 72° C. for 1 min. 30 sec, then 34 cycles of 94° C. for 30 sec., 58° C. for 45 sec., 72° C. for 1 min. 30 sec. The PCR products were subcloned using the pmosBlue PCR cloning system and sequenced.

5' anchored PCR or SLIC strategy (single stranded ligation of cDNA): Specific ss-cDNA was synthesized from human embryonic spinal cord RNA with an antisense primer based on the 3'-extended cDNA sequence: hngn3RT (nucleotides 863–845) 5'-CTGCCAGCCTGG-GAGACTG-3' (SEQ ID NO: 18). Single-stranded DNA was ligated with the A5'-NV: 5'-CTGCATCTATCTAAT-GCTCCTCTCGCTACCTGCTCA CTCTGCGTGA-CATC-3' (SEQ ID NO: 19) as described by Dumas Milne Edwards et al.[29]. Two rounds of nested PCR were performed with the first SLIC primer A5'-1: 5'-GATGT-CACGCAGAGTGAGCAGGTAG-3' (SEQ ID NO: 20) and the specific primer hngn33'-1: (nucleotides 858–836) 5'-AGCCTGGGAGACTGGGGAGTAGA-3' (SEQ ID NO: 21), then with the second SLIC primer A5'-2: 5'-AGAGTGAGCAGGTAGCG AGAGGAG-3' (SEQ ID NO: 22) and the specific primer hngn33'-2: (nucleotides 747–726) 5'-CGCTATGCGCAGCGTTTGAGTC-3' (SEQ ID NO: 23). Both sets of PCR conditions were identical to those used for 3'-anchored PCR. The PCR products were subcloned using the pGemT easy PCR cloning system (Promega) and sequenced.

One of the main expression sites for Relax/ngn3 is the developing spinal cord in rat and mouse[18,19]. Applicants have isolated the human homolog of rodent ngn3 by producing a single-stranded cDNA (ss-cDNA) from mRNA extracted from the spinal cord of a 7-week old human embryo. PCR amplification was performed on the ss-cDNA using primers based on the basic and helix II regions of the Relax/ngn3 sequences. A 138 bp product was amplified (nucleotides 585–722 of SEQ ID NO: 9; see FIG. 3). The sequence of the cloned PCR product was 91.2% and 87.5% identical to the nucleotide sequences of ngn3 and Relax respectively. It was 89.1% identical to the ngn1 and ngn2 sequences. Thus, the isolated PCR fragment is the human homolog of a neurogenin, most probably Relax/ngn3.

To obtain the full-length coding sequence corresponding to the 138 bp PCR fragment, 3'-anchored PCR on human embryonic spinal cord ss-cDNA was performed. A 655 bp PCR fragment was isolated, corresponding to a 3' extension of the original cDNA clone (nucleotides 675–1330 of SEQ ID NO: 9; see FIG. 3). Open reading frame analysis showed that the entire C-terminal region (nucleotides 675–963 of SEQ ID NO: 9) and 366 nucleotides of the 3' untranslated region (nucleotides 964–1330 of SEQ ID NO: 9) had been cloned (FIG. 3). Applicants obtained the 5' end of this cDNA, by performing 5'-anchored PCR by the SLIC method. Applicants amplified a 747 bp PCR fragment (nucleotides 1–747 of SEQ ID NO: 9) that overlapped the 3'-extended cDNA clone over 73 bp (FIG. 3). The two clones were obtained by independent PCR so it was necessary to demonstrate that the contiguous sequence corresponded to a real mRNA and not to a chimera. Applicants demonstrated by reverse transcription-mediated PCR using PCR primers of SEQ ID NO: 24 and SEQ ID NO: 25 that an 1166 bp transcript is present in the human embryonic spinal cord, the sequence of which indeed corresponded to the alignment of the 3' and 5' fragments (nucleotides 1–157 and nucleotides 321–1330 of SEQ ID NO: 9). Nucleotides 158–320 of SEQ ID NO: 9 comprise a 5'-UTR interrupting intron identified by amplification performed on genomic DNA described below. Applicants completely sequenced both strands of four independent PCR products to rule out mutations induced by PCR. The nucleotide sequence was analyzed and the cloned cDNA was found to belong to the neurogenin family, and to be most closely related to Relax/ngn3. Applicants therefore named this cDNA human neurogenin 3 (hngn3).

Figure 4:
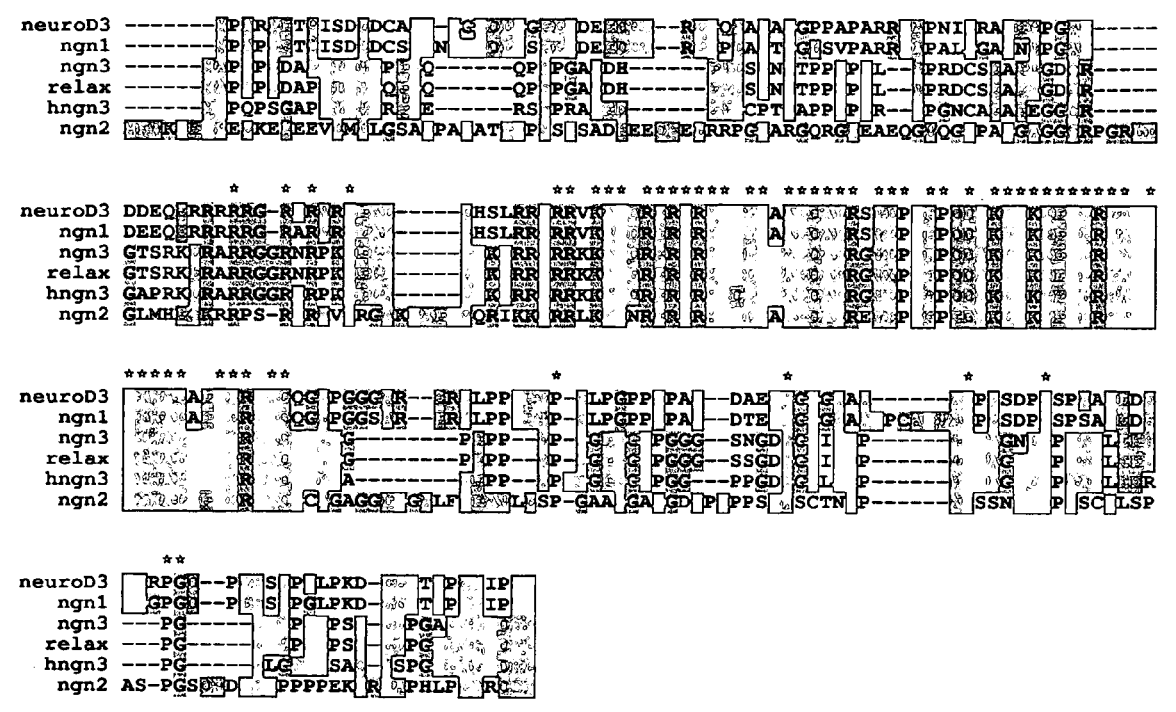

The hngn3 cDNA comprises an open reading frame downstream from an in-frame methionine (FIG. 3). This hngn3 open reading frame is predicted to encode a 214 amino acid polypeptide (SEQ ID NO: 10). Alignment of the predicted amino-acid sequence encoded by hngn3 with the sequences of the mice neurogenins, Relax (rat ngn3) and the human ngn1 homolog (neuroD3) showed that most of the residues of the hngn3 protein were conserved in its murine counterparts. Indeed, hngn3 shares 78.0% and 77.1% identity with Relax and ngn3 respectively whereas only 48%, 46%, and 44% identity is found for neuroD3, ngn1 and ngn2 respectively (FIG. 4).

The genomic sequences of the three mice neurogenin genes and that of the Mash1 gene have been analyzed and the entire coding sequences has been shown to be contained within a single exon[18, 20]. Applicants therefore analyzed the structure of the hngn3 gene by PCR using the set of primers (SEQ ID NO: 24 and SE ID NO: 25) that yielded the 1166 bp fragment in the amplification of spinal cord cDNA. Interestingly, the PCR product obtained from genomic DNA was 1330 bp long and comprised the polynucleotide sequence as depicted in SEQ ID NO: 9. Sequence analysis showed that the coding sequence was contained within a single exon and that there was a 163 bp intron interrupting the 5' untranslated region (nucleotides 158–320 of SEQ ID NO: 9); see FIG. 3). The hngn3 nucleic acid and hngn3 polypeptide sequence information has been deposited within the GenBank/EMBL database (Accession number: AJ133776).

Example 8

Phylogenetic Analysis of the hngn3 Related Sequences

In this Example, Applicants carried out phylogenetic analysis of the relationships between the bHLH factors related to hngn3 and found that the neurogenin genes were homologous to the *Drosophila* Tap gene and did not cluster with the atonal family. This study also shows that a great number of bHLH genes involved in neurogenesis are clearly misnamed.

Optimal alignments of the sequences of the bHLH domains of the proteins most closely related to the protein encoded by our putative human neurogenin3 clone were subjected to phylogenetic analysis with distance methods. The tree obtained was rooted on the *Drosophila* Daughterless protein sequence (FIG. 5a). Five groups were consistently identified, the branching being well supported by the bootstrap values. The vertebrate neurogenin group has the product of the *Drosophila* tap gene as homolog, and is most closely related to the neuroD group, for which no invertebrate homolog has yet been identified. The atonal-related group comprises the nematode lin-32 protein and all the ath1 proteins. These three groups are more distantly related to other sequences of a group consisting of the twist, scleraxis, paraxis, E-hand and D-hand sequences and to the group of the achaete-scute complex. Alignments of whole sequences could only be used for the neurogenin-related sequences (FIG. 5b), and made it possible to depict three paralogous groups in vertebrates, corresponding to ngn1, ngn2 and ngn3 in the mouse. According to this classification, the human gene designated neuroD3 is in fact orthologous to the other ngn1 vertebrate sequences, and the *Xenopus* xngnr1a gene is orthologous to ngn2.

A few key conclusions may be drawn from the phylogenetic analysis. First, various paralogous groups of bHLH proteins were unambiguously defined, thereby helping to clarify the relationships within this transcription factor family (FIG. 4a). All groups except neuroD contained vertebrate and Bilateria representatives (atonal and ath1 proteins, tap and ngn factors, AS-C-related proteins, twist-related factors). *Drosophila* atonal is commonly thought to be the archetype of this group, but the phylogenetic analysis does not support this contention. Atonal does belong to the ath1 group, but it is only distantly related to the neuroD and tap/ngn groups. It is not clear whether neuroD really has no *Drosophila* homolog or whether such a homolog has not yet been found. Four of these groups correspond to proneural or neural specification genes, and it may be that the ancestor genes of this group also had a proneural function that would impose some constraints on the structure-function relationships of the related proteins. Finally, three paralogous proteins belong to the vertebrate ngn subfamily (ngn1, ngn2, and ngn3), although only one is found in metazoans, which diverged much earlier during evolution such as *Drosophila*. This situation is reminiscent of what has been observed for many other family of genes expressed in the CNS, including homeobox proteins, growth factors, enzymes or neurotransmitter receptors[21, 22]. Thus, as in the other gene families, the vertebrate ngn paralogous genes may have been generated by two gene duplications steps that occurred before the emergence of cartilaginous fish and, therefore, all vertebrate groups of species may have at least three representatives of the ngn subfamily of bHLH transcription factors. Finally, a phylogenetic approach should make it possible to unify the system of nomenclature of these proteins, some being clearly misnamed, such as *Xenopus* ngnr1a, human neuroD3, and all the ath proteins (–ath2 to 5) with the exception of the ath1 family.

Example 9

Chromosome Mapping of the hngn3 Gene

Applicants used radiation hybrid mapping, to map the hngn3 gene to chromosome 10q21.3, with a linkage placement confidence of "lodscore>15". Applicants determined the chromosomal location of the hngn3 gene by screening by PCR a panel of human/hamster radiation hybrids (Genebridge 4). Applicants first checked that our PCR conditions resulted in the amplification of a single 1.3 kbp fragment from human genomic DNA whereas no PCR product was obtained from hamster genomic DNA. Applicants then amplified the 1.3 kbp fragment from the genomic DNA of the 93 radiation hybrids. Applicants checked the specificity of the amplification by Southern blot analysis of the resulting PCR products using an internal hngn3 probe.

All PCR primers were chosen with the Oligo 4.0 software program. The nucleotide position of all the primers listed below and the hybridization probe are given relative to the genomic hngn3 sequence (SEQ ID NO: 9). The following primers were used to screen by PCR the Genebridge 4 radiation hybrid panel: hngn3S (nucleotides 1–25): 5'-CCTCGGACCCCATTCTCTCTTCTTT- 3' (SEQ ID NO: 24); hngn3AS (nucleotides 1330–1307): 5'-TGAGTGAGGGTAGGGCGACCCAAG-3' (SEQ ID NO: 25).

PCR was performed with 25 ng of genomic DNA from each radiation hybrid in a final reaction volume of 25 µl containing 0.8 µM of each primer, 200 µM dNTP, 1.5 mM $MgCl_2$, 10 mM Tris, pH 9, 50 mM KCl, 0.1% Triton X-100, 0.01% gelatin and 2 U Taq polymerase. Amplification conditions were: 94° C. for 3 min., 60° C. for 2 min., 72° C. for 1 min, 30 sec, then 29 cycles of 94° C. for 30 sec., 60° C. for 45 sec., 72° C. for 1 min 30 sec.

The PCR products were loaded onto a 1% agarose gel and subjected to electrophoresis. The DNA was then transferred to a HybondN+ membrane (Amersham) under alkaline conditions and probed under standard conditions with a $^{32}$P-labeled hngn3 internal probe: (nucleotides 496–510) 5'-AGGAAGCTCCGGGCA-3' (SEQ ID NO: 26). The membrane was washed several times and autoradiographed.

A specific 1.3 kbp fragment was detected in 24 radiation hybrids of the 93 hybrids in the panel. The PCR results were processed using the Whitehead Institute Radiation Hybrid Mapping software, allowing only lod scores>15 as minimal placement confidence.

Precise chromosomal mapping was performed by linkage analysis using the Whitehead Institute radiation hybrid mapper. Applicants mapped the hngn3 gene to chromosome 10 at 2.74cR from D10S1606 (WI-5300) and 2.53cR from D10S1418 (CHLC.GATA101 E02) with a placement confidence of "lod score>15". Both markers have been mapped to 10q21.3 and according to the Whitehead Institute radiation hybrid map of chromosome 10 they are 3cR apart. Thus, the hngn3 gene maps to the region between the D10S1606 and D10S 1418 markers on the long arm of chromosome 10, and more precisely in position 10q21.3 (FIG. 6).

The hngn3 gene mapped to the long arm of chromosome 10, more precisely to 10q21.3. hngn3 maps to the region encompassing annexin VII (ANX7) to CaM kinase II gamma (CAMKG) and also to that encompassing ankyrin 3 (ANK3) to prosaponin (PSAP). The latter genes have been mapped in either human or mice. In mouse, the ANX7 and CAMKG genes have been mapped in mouse to chromosome 14 whereas the ANK3 and PSAP genes have been mapped to chromosome 10. Thus, the ngn3 gene is probably located in mouse either on chromosome 10 or 14.

Example 10

In Situ Localization of hngn3 Expression in the Human Developing Embryo

In the developing human embryo, Applicants showed by in situ hybridization, that the hngn3 gene is expressed in the spinal cord and pancreas. Furthermore, the expression pattern of hngn3 was identical to that from ngn3 genes in rat and mouse embryos suggesting that the function of ngn3 genes is conserved in mammals.

Human embryos were obtained from legal abortions (Hôpital R. Debré, Professors P. Blot and J. F. Oury, Paris) according to the guidelines of the French Ethical Committee. The embryos were aged from 6 to 7 weeks postconception as determined by crown-to-rump length measured by ultrasound scanning and the Carnegie stage was evaluated according to the general morphology. Embryos were fixed in 4% paraformaldehyde overnight, cryoprotected 48 hours in 1× Phosphate buffered saline (PBS) containing 15% sucrose, embedded in 7% gelatin prepared in 1×PBS with 15% sucrose and frozen in isopentane.

14 µm serial transverse sections were performed and probed with either the antisense (SEQ ID NO: 27) or the sense (SEQ ID NO: 28) digoxygenin-11-UTP labeled hngn3 riboprobes according to the modified whole mount in situ hybridization protocol described by Wilkinson[30]. Negative controls with sense probes did not show any signals.

Figure 7:
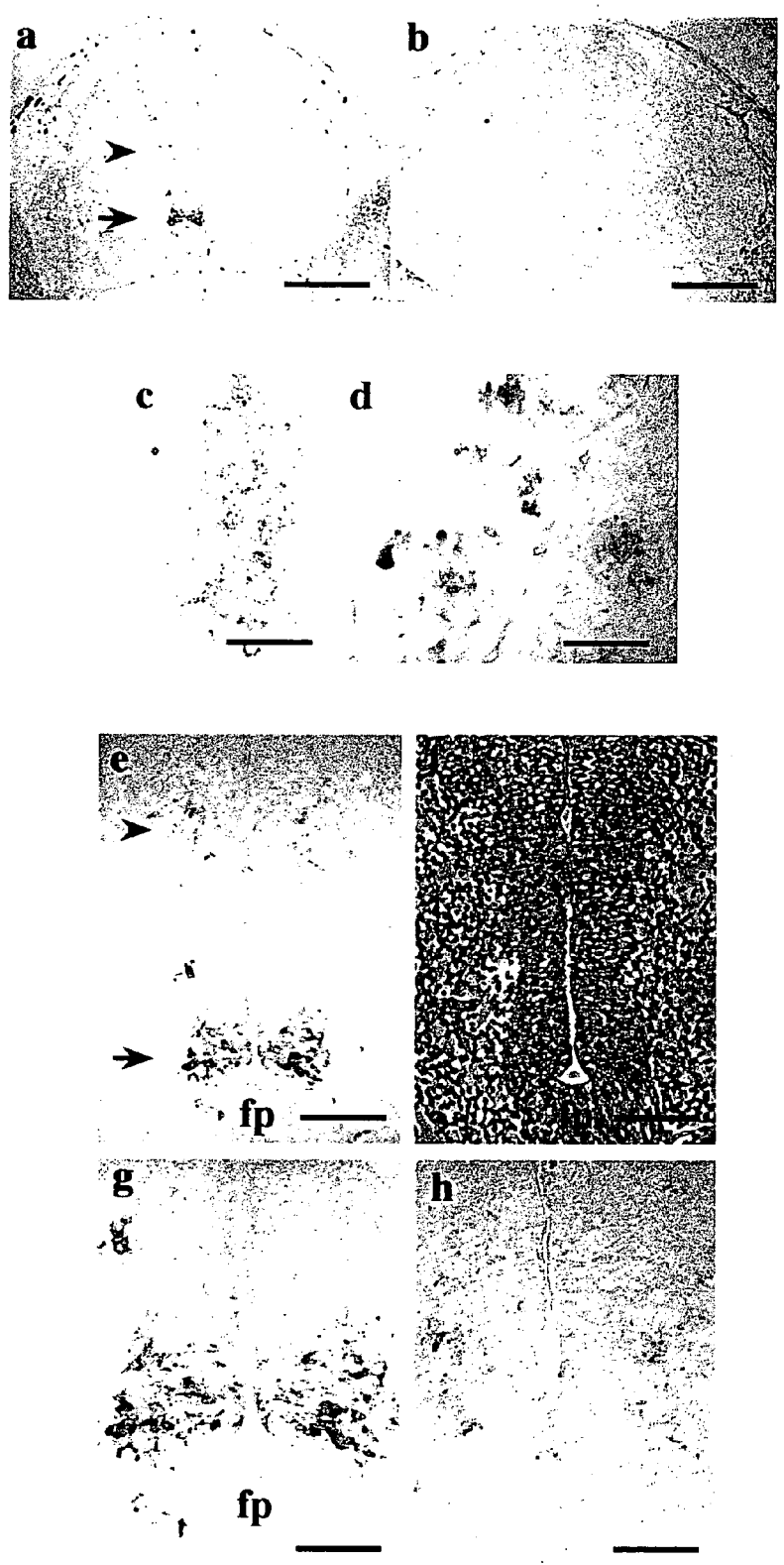
FIGS. 7a–7h: Transverse sections of human embryos at Carnegie stage 18 were probed with an hngn3 antisense riboprobe (a), (c)–(h) and a sense probe (b). In the spinal cord (a), (b), (e)–(h) hngn3-positive cells are present in two longitudinal stripes (a) and (e). The ventral stripe (full arrow) is adjacent to the floor plate (fp). The medial stripe (arrow head) is located around the midpoint of the dorsoventral axis. Both stripes are contained within the ventricular zone as shown by phase contrast microscopy (f). (g) high magnification of the ventral stripe. (h) high magnification of the medial stripe. hngn3 is expressed in scattered cells throughout the pancreas as shown on the transverse section of the left lobe of the pancreas. At higher magnification, the hngn3-positive cells appear to be organized as clusters (d). Scale bars (a) and (b) 200 µm; (c) 100 µm; (e) and (f) 50 µm; (d), (g) and (h) 25 µm.

Transverse sections through human embryos at Carnegie stage 18 (six and a half weeks) were probed with an hngn3 antisense riboprobe. No signal was detected in the negative controls, probed with sense riboprobes (FIG. 7b). hngn3-positive cells were found in the spinal cord and in the pancreas (FIG. 7a, 7c). As previously described for ngn3 in the mouse embryo[18], hngn3 is expressed in scattered cells throughout the pancreas (FIG. 7d). These cells correspond, in the mouse embryo, to the precursors of the islets of Langherans[18]. hngn3 was also expressed in the ventral region of the spinal cord (FIG. 7a, 7e–h), in two longitudinal stripes located at two dorso-ventral positions. The first one is strictly adjacent to the floor plate (FIGS. 7a, 7E and 7g) and the second, with a weaker intensity of staining is located around the midpoint between the floor plate and the roof plate (FIGS. 7a, 7E and 7h). Phase contrast microscopy clearly demonstrated the presence of hngn3-expressing cells inside the ventricular zone of the neural tube (FIG. 7f). In the most ventral stripe, hngn3-positive cells are present near the lumen of the neural tube and in the lateral part of the ventricular zone (FIG. 7g). In the medial stripe, most of the hngn3-expressing cells are located near the marginal border of the ventricular zone (FIG. 7h). This pattern is very similar to that for Relax and ngn3 in the spinal cord of developing rat and mouse embryos[18, 19]. Relax and ngn3 are also expressed in the hindbrain and in the ventral region of the forebrain close to the optic recess[18, 19]. Due to limitations inherent in the use of human embryos, all the samples collected were extensively damaged at the anterior part. Thus, histological analysis was not possible for the hindbrain or the forebrain. Nevertheless, Applicants found that hngn3 was expressed in the same compartments as Relax and ngn3 in the pancreas and the spinal cord. Our results suggest a conservation of function for the neurogenin 3 genes of humans, mice and rats.

The expression pattern of hngn3 in the spinal cord is identical to that of Relax in rats and ngn3 in mice[18, 19]. In the pancreas, hngn3 expressing cells were found in clusters similar to those described in the mouse pancreas[18]. Several lines of evidence support the idea that ngn3 governs the differentiation of the endocrine pancreas. Firstly, Sommer et al.[18] have shown that the expression of ngn3 and neuroD is coordinated both in space and time suggesting that ngn3 controls neuroD expression. Secondly, mice carrying a null mutation in the neuroD gene have severe diabetes[23]. Mutant mice have far fewer insulin-producing β-cells and do not develop mature islets. Finally, it is most likely that ngn3 initiates the differentiation of pancreatic β-cells by controlling the expression of neuroD and the subsequent production of insulin[23]. More recent data has demonstrated that ngn3 is the gene that controls the entire differentiation of the endocrine pancreas. Analysis of ngn mutant mice has shown that these mice lack the four pancreatic endocrine cell types (including the insulin producing cells).[31] In addition, it has been demonstrated that the overexpression of ngn3 in the developing pancreas yields an increased number of endocrine cells.[32] Thus, any mutations in the hngn3 gene could lead to severe diabetes. The hngn3 gene has been mapped to the 10q21.3 position. In this region, no genes for inheritable diseases with phenotypes consistent with a hngn3-altered function have been identified. The numerous studies performed on the genetic predisposition to type 1 diabetes mellitus have shown polygenic inheritance of the disease with a major locus at the major histocompatibility complex (MHC)[24, 25]. The various susceptibility loci outside the MHC locus remain to be identified. hngn3 is a strong candidate gene for the yet unmapped genes for insulin-dependent diabetes. It may also be involved in other human diseases. Rostomily et al.[26] have shown that the human neurogenin 1 homolog gene, NeuroD3, is expressed in primitive neuroectodermal tumors, especially in those that are highly metastatic. Thus, the analysis of hngn3 expression in neuroectodermal tumors and in pancreatic b-cells tumors, such as insulinomas, may indicate whether the disregulation of the hngn3 gene is involved in malignant transformation.

The human homolog of neurogenin 3 (hngn3) from human embryonic spinal cord has been now been identified by Applicants. Phylogenetic analysis showed that the neurogenin genes are homologous to the *Drosophila* Tap gene and that the atonal gene is certainly not the archetype of this gene family as was previously suggested. A radiation hybrid panel was screened, leading to the mapping of the hngn3 gene to the 10q210.3 position. Early human embryos were used to investigate the pattern of hngn3 expression. Most importantly, the cells expressing hngn3 were located in the same compartments of the spinal cord and pancreas as those expressing ngn3 genes in rats and mice. Thus, these data support the idea of a functional conservation among the neurogenin 3 genes.

The structure of the various neurogenin genes appears to be conserved, with, as described here for the hngn3 gene, the entire coding sequence contained within a single exon. Similar genomic organizations have been reported for the other three mouse ngn genes, the Zebrafish ngn1 gene and the mouse Mash1 gene[12, 18, 20]. The identification of a single intron interrupting the 5' untranslated region of the hngn3 gene is similar to the organization of that of two other members of the ngn family, the mouse ngn2 and Zebrafish ngn1 genes[12, 16]. The structures of the other known neurogenins have not yet been fully analyzed. However, the presence of an intron within the 5'UTR and the absence of introns within the coding region may be common features of neurogenin genes.

ABBREVIATIONS bp: base pairs, kbp: kilo base pairs, cR: centiRays

REFERENCES

1. D. Srivastava, P. Cserjesi and E. N. Olson (1995). A subclass of bHLH proteins required for cardiac morphogenesis. *Science* 270, 1995–1999.
2. P. Cserjesi, D. Brown, K. L. Ligon, G. E. Lyons, N. G. Copeland, D. J. Gilbert, N. A. Jenkins and E. N. Olson (1995). Scleraxis: a basic helix-loop-helix protein that prefigures skeletal formation during mouse embryogenesis. *Development* 121, 1099–1110.
3. R. Burgess, P. Cserjesi, K. L. Ligon and E. N. Olson (1995). Paraxis: a basic helix-loop-helix protein expressed in paraxial mesoderm and developing somites. *Dev. Biol.* 168, 296–306.
4. L. Li, P. Cserjesi and E. N. Olson (1995). Dermo-1: a novel twist-related bHLH protein expressed in the developing dermis. Dev. Biol. 172, 280–292.
5. H. Weintraub (1993). The MyoD family and myogenesis: redundancy, networks and thresholds. *Cell* 75, 1241–1244.
6. Y. N. Jan and L. Y. Jan (1993). HLH proteins, Fly neurogenesis and vertebrate myogenesis. *Cell* 75, 827–830.
7. S. Campuzano and J. Modolell (1992). Patterning of *drosophila* nervous system: The achaete-scutel gene complex. *Trends in Genetics* 8, 202–208.
8. P. Simpson (1997). Notch signaling in development: on equivalence groups and asymmetric developmental potential. *Curr. Opin. Genet. Dev.* 7, 537–542.
9. S. Artavanis-Tsakonas, K. Matsuno and M. E. Fortini (1995). Notch signalling. *Science* 267, 225–232.
10. J. E. Lee (1997). Basic helix-loop-helix genes in neural development. *Development* 124, 1611–21.
11. Q. Ma, C. Kintner and D. J. Anderson (1996). Identification of neurogenin, a vertebrate neuronal determination gene. *Dev Biol* 180, 227–41.

12. P. Blader, N. Fischer, G. Gradwohl, F. Guillemont and U. Strahle (1997). The activity of neurogenin1 is controlled by local cues in the zebrafish embryo. *Development* 124, 4557–69.
13. P. Kim, A. W. Helms, J. E. Johnson and K. Zimmerman (1997). XATH-1, a vertebrate homolog of *Drosophila* atonal, induces a neuronal differentiation within ectodermal progenitors. *Cancer Res* 57, 3526–31.
14. P. Ravassard, J. Vallin, J. Mallet and C. Icard-Liepkalns (1997). Relax promotes ectopic neuronal differentiation in *Xenopus* embryos. *Proc Natl Acad Sci U S A* 94, 8602–5.
15. E. Cau, G. Gradwohl, C. Fode and F. Guillemot (1997). Mash1 activates a cascade of bHLH regulators in olfactory neuron progenitors. Development 124, 1611–21.
16. C. Fode, G. Gradwohl, X. Morin, A. Dierich, M. LeMeur, C. Goridis and F. Guillemot (1998). The bHLH protein NEUROGENIN 2 is a determination factor for epibranchial placode-derived sensory neurons. *Neuron* 20, 483–94.
17. Q. Ma, Z. Chen, del, Barco, Barrantes, I, de, la, Pompa, Jl and D. J. Anderson (1998). neurogenin1 is essential for the determination of neuronal precursors for proximal cranial sensory ganglia. *Neuron* 20, 483–94.
18. L. Sommer, Q. Ma and D. J. Anderson (1996). neurogenins, a novel family of atonal-related bHLH transcription factors, are putative mammalian neuronal determination genes that reveal progenitor cell heterogeneity in the developing CNS and PNS. *Cell* 87, 43–52.
19. P. Ravassard, F. Chatail, J. Mallet and C. Icard-Liepkalns (1997). Relax, a novel rat bHLH transcriptional regulator transiently expressed in the ventricular proliferating zone of the developing central nervous system. *J Neurosci Res* 48, 146–58.
20. F. Guillemot, L. C. Lo, J. E. Johnson, A. Auerbach and D. J. Anderson (1993). Mammalian achaete-scute homolog 1 is required for the early development of olfactory and autonomic neurons. *Cell* 75, 1245–1258.
21. B. Cardinaud, J. M. Gilbert, F. Liu, K. S. Sugamori, J. D. Vincent, H. B. Niznik and P. Vernier (1998). Evolution and origin of the diversity of dopamine receptors in vertebrates. *Adv Pharmacol* 42, 936–40.
22. A. C. Sharman and P. W. Holland (1998). Estimation of Hox gene cluster number in lampreys. *Int J Dev Biol* 42, 617–20.
23. F. J. Naya, H. P. Huang, Y. Qiu, H. Mutoh, F. J. DeMayo, A. B. Leiter and M. J. Tsai (1997). Diabetes, defective pancreatic morphogenesis, and abnormal enteroendocrine differentiation in BETA2/neuroD-deficient mice. *Genes Dev* 11, 2323–34.
24. R. Buzzetti, C. C. Quattrocchi and L. Nistico (1998). Dissecting the genetics of type 1 diabetes: relevance for familial clustering and differences in incidence. *Diabetes Metab Rev* 14, 111–28.
25. C. Julier, L. Hashimoto and G. M. Lathrop (1996). Genetics of insulin-dependent diabetes mellitus. *Curr Opin Genet Dev* 6, 354–60.
26. R. C. Rostomily, M. O. Bermingham, M. S. Berger, S. J. Tapscott, T. A. Reh and J. M. Olson (1997). Expression of neurogenic basic helix-loop-helix genes in primitive neuroectodermal tumors. *Development* 124, 4557–69.
27. P. Chomczynski and N. Sacchi (1987). Single-step method of RNA isolation by acid guanidinium thiocyanate-phenol-chloroform extraction. *Anal Biochem* 162, 156–9.
28. P. Ravassard, C. Icard-Liepkalns, J. Mallet, and J. B. Dumas Milne Edwards (1997). cDNA libraries from a low amount of cells. *Methods Mol Biol* 67, 317–29.
29. J. B. Dumas Milne Edwards, P. Ravassard, C. Icard-Liepkalns and J. Mallet. (1995). cDNA cloning by RT-PCR. In PCR2: A practical approach, M. J. McPherson, B. D. Hames and G. R. Taylor, eds. (Oxford, U.K.: IRL Press), pp. 89–118.
30. A. G. Wilkinson. (1994). Whole mount in situ hybridization of vertebrate embryos. In: In situ hybridization: A practical approach, D. G. Wilkinson, ed. (Oxford, U.K.: IRL Press), pp. 75–83.
31. Gradwohl G. Dierich A, LeMeur M, Guillemot F. neurogenin3 is required for the development of four cell lineages of the pancreas. Proc Natl Acad Sci USA. 2000 Feb. 15; 97(4):1607–11.
32. Apelqvist A, Li H, Sommer L, Beatus P, Anderson D J, Honjo T, Hrabe de Angelis M, Lendahl U and Edlund, H. Notch signalling controls pancreatic cell differentation. Nature. 1999 Aug. 26; 400(6747):877–81.

The invention claimed is:

1. An isolated nucleic acid comprising a polynucleotide sequence as depicted in SEQ ID NO: 1, or a complementary polynucleotide sequence of said isolated nucleic acid.

2. The isolated nucleic acid according to claim 1, wherein the nucleic acid further comprises a marker nucleotide sequence.

3. A recombinant vector comprising the nucleic acid according to claim 1.

4. The recombinant vector according to claim 3, wherein the recombinant vector is an adenovirus.

5. A recombinant host cell comprising the recombinant vector according to claim 3.

6. A composition comprising the recombinant vector according to claim 3 and an excipient.

7. A recombinant host cell comprising the nucleic acid according to claim 1.

8. A composition comprising the nucleic acid according to claim 1 and an excipient.

9. A nucleotide probe specific for a neurogenin 3 (ngn3) nucleic acid, wherein the nucleotide probe comprises the complementary polynucleotide sequence of SEQ ID NO: 1.

10. An isolated nucleic acid encoding a polypeptide comprising an amino acid sequence of SEQ ID NO: 10.

11. A recombinant vector comprising the nucleic acid according to claim 10.

12. A recombinant host cell comprising the recombinant vector according to claim 11.

13. A composition comprising the recombinant host cell according to claim 12 and an excipient.

14. A composition comprising the recombinant vector according to claim 11 and an excipient.

15. A recombinant host cell comprising the nucleic acid according to claim 10.

16. A composition comprising the recombinant host cell according to claim 15 and an excipient.

17. A composition comprising the nucleic acid according to claim 10 and an excipient.

* * * * *